(12) United States Patent
Martin et al.

(10) Patent No.: US 7,811,585 B2
(45) Date of Patent: *Oct. 12, 2010

(54) STREPTOCOCCUS PYOGENES ANTIGENS

(75) Inventors: Denis Martin, Ste-Therese (CA); Josee Hamel, Sillery (CA); Bernard Brodeur, Sillery (CA); Stephane Rioux, Ohain (BE); Martine Boyer, Ste-Foy (CA)

(73) Assignee: ID Biomedical Corporation, Laval (CA)

( * ) Notice: Subject to any disclaimer, the term of this patent is extended or adjusted under 35 U.S.C. 154(b) by 177 days.

This patent is subject to a terminal disclaimer.

(21) Appl. No.: 11/775,131

(22) Filed: Jul. 9, 2007

(65) Prior Publication Data

US 2008/0038268 A1    Feb. 14, 2008

Related U.S. Application Data

(63) Continuation of application No. 10/332,231, filed as application No. PCT/CA01/01001 on Jul. 6, 2001, now Pat. No. 7,247,308.

(60) Provisional application No. 60/216,465, filed on Jul. 6, 2000.

(51) Int. Cl.
*A61K 39/02* (2006.01)

(52) U.S. Cl. .............. 424/243.1; 424/185.1; 424/190.1; 435/7.1; 435/7.32; 530/350

(58) Field of Classification Search ........................ None
See application file for complete search history.

(56) References Cited

U.S. PATENT DOCUMENTS 7,247,308 B2    7/2007    Martin et al. ............ 424/244.1

FOREIGN PATENT DOCUMENTS

EP    0916726 A1    5/1999

WO    WO 02/04495 A3    1/2002

OTHER PUBLICATIONS

Greenspan et al (Nature Biotechnology 7: 936-937, 1999).*
Chothia et al (The EMBO Journal, 1986, 5/4:823-26).*
Database EMBL/Genbank/DDBJ 'Online! EBI; Aug. 5, 1994, "42 KDa protein (ORF1) and 67 KDa myosin-crossreactive streptococcal antigen gene, complete cds," XP002194339, Acc. No. SP09352.
Database Swall 'Online! EBI; Jun. 1, 2001, "Putative 42 KDa protein of S. pyogenes (encoded by gene spy0469)," XP002194340, Acc. No. Q9A147.
Database Swall 'Online! EBI; Nov. 1, 1996, "42 KDa protein (ORFI) and 67 KDa myosin-crossreactive streptococcal antigen," XP002194338, Acc. No. Q54524.
Kil et al., "Cloning and Sequence Analysis of a Gene Encoding a 67-Kilodalton Myosin-Cross-Reactive Antigen of *Streptococcus pyogenes* Reveals Its Similarity with Class II Major Histocompatibility Antigens," *Infection and Immunity* 62(6): 2440-2449, Jun. 1994.
Mikayama et al., "Molecular cloning and functional expression of a cDNA encoding glycosylation-inhibiting factor," *Proc. Natl. Acad. Sci. USA 90*: 10056-10060, Nov. 1993.
Rudinger, "Characteristics of the amino acids as components of a peptide hormone sequence," *Peptide Hormones Biol. Council*, pp. 5-7, Jun. 1976.
Hopp, "Retrospective: 12 Years of Antigenic Determinant Predictions, and More," *Peptide Research* 6(4):183-190, 1993.
Jameson et al., "The antigenic index: a novel algorithm for predicting antigenic determinants," *Computer Application Bioscience* 4(1):181-186, 1988.
Kolaskar et al., "A semi-empirical method for prediction of antigenic determinants on protein antigens," *FEBS* 276(1,2): 172-174, 1990.
Menéndez-Arias et al., "A Basic microcomputer program for prediction of B and T cell epitopes in proteins," *Comput. Appl. Biosci.* 6(2):101-105, 1990.

* cited by examiner

*Primary Examiner*—Jennifer E Graser
(74) *Attorney, Agent, or Firm*—Seed IP Law Group PLLC

(57) ABSTRACT

The present invention relates to antigens, more particularly an antigen of *Streptococcus pyogenes* (also called group A *Streptococcus* (GAS)) bacterial pathogen which is useful as vaccine component for therapy and/or prophylaxis.

7 Claims, 13 Drawing Sheets

Figure 1

```
   1 ATGATTATTA CTAAAAAGAG CTTATTTGTG ACAAGTGTCG CTTTGTCGTT AGCACCTTTG
  61 GCGACAGCAC AGGCACAAGA GTGGACACCA CGATCGGTTA CAGAAATCAA GTCTGAACTC
 121 GTCCTAGTTG ATAATGTTTT TACTTATACT GTAAAATACG GTGACACTTT AAGCACAATT
 181 GCTGAAGCAA TGGGAATTGA TGTGCATGTC TTAGGAGATA TTAATCATAT TGCTAATATT
 241 GACTTAATTT TTCCAGACAC GATCCTAACA GCCAACTACA ACCAACACGG TCAGGCAACG
 301 ACTTTGACGG TTCAAGCGCC TGCTTCTAGT CCAGCTAGCG TTAGTCATGT ACCTAGCAGT
 361 GAGCCATTAC CCAAGCATC TGCCACCTCT CAATCGACTG TTCCTATGGC ACCATCTGCG
 421 ACACCATCTG ATGTCCCAAC GACACCATTC GCATCTGCAA AGCCAGATAG TTCTGTGACA
 481 GCGTCATCTG AGCTCACATC GTCAACGAAT GATGTTTCGA CTGAGTTGTC TAGCGAATCA
 541 CAAAAGCAGC CAGAAGTACC ACAAGAAGCA GTTCCAACTC CTAAAGCAGC TGAAACGACT
 601 GAAGTCGAAC CTAAGACAGA CATCTCAGAG GATTCAACTT CAGCTAATAG GCCTGTACCT
 661 AACGAGAGTG CTTCAGAAGA AGTTTCTTCT GCGGCCCCAG CACAAGCCCC AGCAGAAAAA
 721 GAAGAAACCT CTGCGCCAGC AGCACAAAAA GCTGTAGCTG ACACCACAAG TGTTGCAACC
 781 TCAAATGGCC TTTCTTACGC TCCAAACCAT GCCTACAATC CAATGAATGC AGGGCTTCAA
 841 CCACAAACAG CAGCCTTCAA AGAAGAAGTG GCTTCTGCCT TTGGTATTAC GTCATTTAGT
 901 GGTTACCGTC CAGGTGATCC AGGAGATCAT GGTAAAGGTT TGGCCATTGA TTTTATGGTG
 961 CCTGAAAATT CTGCTCTTGG TGATCAAGTT GCTCAATATG CCATTGACCA TATGGCAGAG
1021 CGTGGTATTT CATACGTTAT TTGGAAACAG CGATTCTATG CGCCATTTGC AAGTATTTAC
1081 GGACCAGCCT ACACATGGAA CCCCATGCCA GATCGCGGCA GTATTACAGA AAACCATTAT
1141 GATCATGTTC ATGTCTCCTT TAATGCTTAA (SEQ ID NO:1)
```

Figure 2

```
  1 MIITKKSLFV TSVALSLAPL ATAQAQEWTP RSVTEIKSEL VLVDNVFTYT VKYGDTLSTI
 61 AEAMGIDVHV LGDINHIANI DLIFPDTILT ANYNQHGQAT TLTVQAPASS PASVSHVPSS
121 EPLPQASATS QSTVPMAPSA TPSDVPTTPF ASAKPDSSVT ASSELTSSTN DVSTELSSES
181 QKQPEVPQEA VPTPKAAETT EVEPKTDISE DSTSANRPVP NESASEEVSS AAPAQAPAEK
241 EETSAPAAQK AVADTTSVAT SNGLSYAPNH AYNPMNAGLQ PQTAAFKEEV ASAFGITSFS
301 GYRPGDPGDH GKGLAIDFMV PENSALGDQV AQYAIDHMAE RGISYVIWKQ RFYAPFASIY
361 GPAYTWNPMP DRGSITENHY DHVHVSFNA* (SEQ ID NO:2)
```

Figure 3

```
   1 ATGATTATTA CTAAAAAGAG CTTATTTGTG ACAAGTGTCG CTTTGTCGTT AGCACCTTTG
  61 GCGACAGCGC AGGCACAAGA GTGGACACCA CGATCGGTTA CAGAAATCAA GTCTGAACTC
 121 GTCCTAGTTG ATAATGTTTT TACTTATATA GTAAAATACG GTGACACTTT AAGCACAATT
 181 GCTGAAGCAA TGGGGATTGA TGTGCATGTC TTAGGAGATA TTAATCATAT TGCTAATATT
 241 GACTTAATTT TTCCAGACAC GATCCTAACA GCAAACTACA ACCAACACGG TCAGGCAACG
 301 ACTTTGACGG TTCAAGCACC TGCTTCTAGT CCATCTAGCG TTAGTCATGT ACCTAGCAGT
 361 GAGCCATTAC CCCAAGCATC TGCCACCTCT CAACCGACTG TTCCTATGGC ACCATCTGCG
 421 ACACCATCTG ATGTCCCAAC GACACCATTC GCATCTGCAA AGCCAGATAG TTCTGTGACA
 481 GCGTCATCTG AGCTCACATC GTCAACGAAT GATGTTTCGA CTGAGTTGTC TAGCGAATCA
 541 CAAAAGCAGC CAGAAGTACC ACAAGAAGCA GTTCCAACTC CTAAAGCAGC TGAACCGACT
 601 GAAGTCGAAC CTAAGACAGA CATCTCAGAA GACCCAACTT CAGCTAATAG GCCTGTACCT
 661 AACGAGAGTG CTTCAGAAGA AGCTTCTTCT GCGGCCCCAG CACAAGCTCC AGCAGAAAAA
 721 GAAGAAACCT CTCAGATGTT AACTGCGCCA GCAGCACAAA AAGCTGTAGC TGACACCACA
 781 AGTGTTGCAA CCTCAAACGG CCTTTCTTAC GCTCCAAACC ATGCCTACAA TCCAATGAAT
 841 GCAGGGCTTC AACCACAAAC AGCAGCCTTC AAAGAAGAAG TGGCTTCTGC CTTTGGTATT
 901 ACGTCATTTA GTGGTTACCG TCCAGGAGAT CCAGGAGATC ATGGTAAAGG ATTAGCCATT
 961 GACTTTATGG TACCGGTTAG CTCTACGCTT GGTGATCAAG TTGCTCAATA TGCCATTGAC
1021 CATATGGCAG AGCGTGGTAT TTCATACGTT ATTTGGAAAC AGCGATTCTA TGCGCCATTT
1081 GCAAGTATTT ACGGACCAGC CTACACATGG AACCCCATGC CAGATCGCGG CAGTATTACA
1141 GAAAACCATT ATGATCATGT TCATGTCTCC TTTAATGCTT AA (SEQ ID NO:3)
```

Figure 4

```
   1 MIITKKSLFV TSVALSLAPL ATAQAQEWTP RSVTEIKSEL VLVDNVFTYI VKYGDTLSTI
  61 AEAMGIDVHV LGDINHIANI DLIFPDTILT ANYNQHGQAT TLTVQAPASS PSSVSHVPSS
 121 EPLPQASATS QPTVPMAPSA TPSDVPTPF ASAKPDSSVT ASSELTSSTN DVSTELSSES
 181 QKQPEVPQEA VPTPKAAEPT EVEPKTDISE DPTSANRPVP NESASEEASS AAPAQAPAEK
 241 EETSQMLTAP AAQKAVADTT SVATSNGLSY APNHAYNPMN AGLQPQTAAF KEEVASAFGI
 301 TSFSGYRPGD PGDHGKGLAI DFMVPVSSTL GDQVAQYAID HMAERGISYV IWKQRFYAPF
 361 ASIYGPAYTW NPMPDRGSIT ENHYDHVHVS FNA* (SEQ ID NO:4)
```

Figure 5

```
   1 ATGATTATTA CTAAAAAGAG CTTATTTGTG ACAAGTGTCG CTTTGTCGTT AGTACCTTTG
  61 GCGACAGCGC AGGCACAAGA GTGGACACCA CGATCGGTTA CAGAAATCAA GTCTGAACTC
 121 GTCCTAGTTG ATAATGTTTT TACTTATACT GTAAAATACG GTGACACTTT AAGCACAATT
 181 GCTGAAGCAA TGGGGATTGA TGTGCATGTC TTAGGAGATA TTAATCATAT TGCTAATATT
 241 GACCTAATTT TTCCAGACAC GATCCTAACA GCAAACTACA ATCAACACGG TCAGGCAACG
 301 AATTTGACGG TTCAAGCACC TGCTTCTAGT CCAGCTAGCG TTAGTCATGT ACCTAGCAGT
 361 GAGCCATTAC CCCAAGCATC TGCCACCTCT CAACCGACTG TTCCTATGGC ACCACCTGCG
 421 ACACCATCTG ATGTCCCAAC GACACCATTC GCATCTGCAA AGCCAGATAG TTCTGTGACA
 481 GCGTCATCTG AGCTCACATC GTCAACGAAT GATGTTTCGA CTGAGTTGTC TAGCGAATCA
 541 CAAAAGCAGC CAGAAGTACC ACAAGAAGCA GTTCCAACTC CTAAAGCAGC TGAAACGACT
 601 GAAGTCGAAC CTAAGACAGA CATCTCAGAA GCCCCAACTT CAGCTAATAG GCCTGTACCT
 661 AACGAGAGTG CTTCAGAAGA AGTTTCTTCT GCGGCCCCAG CACAAGCCCC AGCAGAAAAA
 721 GAAGAAACCT CTGCGCCAGC AGCACAAAAA GCTGTAGCTG ACACCACAAG TGTTGCAACC
 781 TCAAATGGCC TTTCTTACGC TCCAAACCAT GCCTACAATC CAATGAATGC AGGGCTTCAA
 841 CCACAAACAG CAGCCTTCAA AGAAGAAGTG GCTTCTGCCT TTGGTATTAC GTCATTTAGT
 901 GGTTACCGTC CAGGTGATCC AGGAGATCAT GGTAAAGGTT TGGCCATTGA TTTTATGGTG
 961 CCTGAAAATT CTGCTCTTGG TGATCAAGTT GCTCAATATG CCATTGACCA TATGGCAGAG
1021 CGTGGTATTT CATACGTTAT TTGGAAACAG CGATTCTATG CGCCATTTGC AAGTATTTAC
1081 GGACCAGCCT ACACATGGAA CCCCATGCCA GATCGCGGCA GTATTACAGA AAACCATTAT
1141 GATCATGTTC ATGTCTCCTT TAATGCTTAA (SEQ ID NO:5)
```

Figure 6

```
   1 MIITKKSLFV TSVALSLVPL ATAQAQEWTP RSVTEIKSEL VLVDNVFTYT VKYGDTLSTI
  61 AEAMGIDVHV LGDINHIANI DLIPPDTILT ANYNQHGQAT NLTVQAPASS PASVSHVPSS
 121 EPLPQASATS QPTVPMAPPA TPSDVPTTPF ASAKPDSSVT ASSELTSSTN DVSTELSSES
 181 QKQPEVPQEA VPTPKAAETT EVEPKTDISE APTSANRPVP NESASEEVSS AAPAQAPAEK
 241 EETSAPAAQK AVADTTSVAT SNGLSYAPNH AYNPMNAGLQ PQTAAFKEEV ASAFGITSFS
 301 GYRPGDPGDH GKGLAIDFMV PENSALGDQV AQYAIDHMAE RGISYVIWKQ RFYAPFASIY
 361 GPAYTWNPMP DRGSITENHY DHVHVSFNA* (SEQ ID NO:6)
```

Figure 7

```
   1 ATGATTATTA CTAAAAAGAG CTTATTTGTG ACAAGTGTCG CTTTGTCGTT AGCACCTTTG
  61 GCGACAGCGC AGGCACAAGA GTGGACACCA CGATCGGTTA CAGAAATCAA GTCTGAACTC
 121 GTCCTAGTTG ATAATGTTTT TACTTATACA GTAAAATACG GTGACACTTT AAGCACAATT
 181 GCTGAAGCAA TGGGGATTGA TGTGCATGTC TTAGGAGATA TTAATCATAT TGCTAATATT
 241 GACTTAATTT TTCCAGACAC GATCCTAACA GCAAACTACA ATCAACACGG TCAGGCAACG
 301 ACTTTGACGG TTCAAGCACC TGCTTCTAGT CCAGCTAGCG TTAGTCATGT ACCTAGCAGT
 361 GAGCCATTAC CCCAAGCATC TGCCACCTCT CAACCGACTG TTCCTATGGC ACCATCTGCG
 421 ACACCATTAG CATCTGCAAA GCCAGATAGT TCTGTGACAG CGTCATCTGA GCTCACATCG
 481 TCAACGAATG ATGTTTCGAC TGAGTCGTCT AGCGAATCAC AAAAGCAGCC AGAAGTACCA
 541 CAAGAAGCAG TTCCAACTCC TAAAGCAGCT GAAACGACTG AAGTCGAACC TAAGACAGAC
 601 ATCTCAGAAG ACCCAACTTC AGCTAATAGG CCTGTACCTA ACGAGAGTGC TTCAGAAGAA
 661 GTTTCTTCTG CGGCCCCAGC ACAAGCCCCA GCAGAAAAAG AAGAAACCTC TGCCGCAGCA
 721 GCACAAAAAG CTGTAGCTGA CACCACAAGT GTTGCAACCT CAAACGGCCT TTCTTACGCT
 781 CCAAACCATG CCTACAATCC AATGAATGCA GGGCTTCAAC CACAAACAGC AGCCTTCAAA
 841 GAAGAAGTGG CTTCTGCCTT TGGTATTACG TCATTTAGTG GTTACCGTCC AGGTGACCCA
 901 GGAGATCATG GTAAAGGTTT GGCCATTGAT TTTATGGTGC CTGAAAATTC TGCTCTTGGT
 961 GATCAAGTTG CTCAATATGC CATTGACCAT ATGGCAGAGC GTGGTATTTC ATACGTTATT
1021 TGGAAACAGC GATTCTATGC GCCATTTGCA AGTATTTACG GACCAGCTTA CACATGGAAC
1081 CCCATGCCAG ATCGCGGCAG TATTACAGAA AACCATTATG ATCATGTTCA TGTCTCCTTT
1141 AATGCTTAA (SEQ ID NO:7)
```

Figure 8

```
   1 MIITKKSLFV TSVALSLAPL ATAQAQEWTP RSVTEIKSEL VLVDNVFTYT VKYGDTLSTI
  61 AEAMGIDVHV LGDINHIANI DLIFPDTILT ANYNQHGQAT TLTVQAPASS PASVSHVPSS
 121 EPLPQASATS QPTVPMAPSA TPLASAKPDS SVTASSELTS STNDVSTESS SESQKQPEVP
 181 QEAVPTPKAA ETTEVEPKTD ISEDPTSANR PVPNESASEE VSSAAPAQAP AEKEETSAPA
 241 AQKAVADTTS VATSNGLSYA PNHAYNPMNA GLQPQTAAFK EEVASAFGIT SFSGYRPGDP
 301 GDHGKGLAID FMVPENSALG DQVAQYAIDH MAERGISYVI WKQRFYAPFA SIYGPAYTWN
 361 PMPDRGSITE NHYDHVHVSF NA* (SEQ ID NO:8)
```

Figure 9

```
1    CAAGAGTGGA CACCACGATC GGTTACAGAA ATCAAGTCTG AACTCGTCCT AGTTGATAAT
61   GTTTTTACTT ATACTGTAAA ATACGGTGAC ACTTTAAGCA CAATTGCTGA AGCAATGGGA
121  ATTGATGTGC ATGTCTTAGG AGATATTAAT CATATTGCTA ATATTGACTT AATTTTTCCA
181  GACACGATCC TAACAGCCAA CTACAACCAA CACGGTCAGG CAACGACTTT GACGGTTCAA
241  GCGCCTGCTT CTAGTCCAGC TAGCGTTAGT CATGTACCTA GCAGTGAGCC ATTACCCCAA
301  GCATCTGCCA CCTCTCAATC GACTGTTCCT ATGGCACCAT CTGCGACACC ATCTGATGTC
361  CCAACGACAC CATTCGCATC TGCAAAGCCA GATAGTTCTG TGACAGCGTC ATCTGAGCTC
421  ACATCGTCAA CGAATGATGT TTCGACTGAG TTGTCTAGCG AATCACAAAA GCAGCCAGAA
481  GTACCACAAG AAGCAGTTCC AACTCCTAAA GCAGCTGAAA CGACTGAAGT CGAACCTAAG
541  ACAGACATCT CAGAGGATTC AACTTCAGCT AATAGGCCTG TACCTAACGA GAGTGCTTCA
601  GAAGAAGTTT CTTCTGCGGC CCCAGCACAA GCCCCAGCAG AAAAAGAAGA AACCTCTGCG
661  CCAGCAGCAC AAAAAGCTGT AGCTGACACC ACAAGTGTTG CAACCTCAAA TGGCCTTTCT
721  TACGCTCCAA ACCATGCCTA CAATCCAATG AATGCAGGGC TTCAACCACA AACAGCAGCC
781  TTCAAAGAAG AAGTGGCTTC TGCCTTTGGT ATTACGTCAT TTAGTGGTTA CCGTCCAGGT
841  GATCCAGGAG ATCATGGTAA AGGTTTGGCC ATTGATTTTA TGGTGCCTGA AAATTCTGCT
901  CTTGGTGATC AAGTTGCTCA ATATGCCATT GACCATATGG CAGAGCGTGG TATTTCATAC
961  GTTATTTGGA AACAGCGATT CTATGCGCCA TTTGCAAGTA TTTACGGACC AGCCTACACA
1021 TGGAACCCCA TGCCAGATCG CGGCAGTATT ACAGAAAACC ATTATGATCA TGTTCATGTC
1081 TCCTTTAATG CTTAA (SEQ ID NO:9)
```

Figure 10

```
1    QEWTPRSVTE IKSELVLVDN VFTYTVKYGD TLSTIAEAMG IDVHVLGDIN HIANIDLIFP
61   DTILTANYNQ HGQATTLTVQ APASSPASVS HVPSSEPLPQ ASATSQSTVP MAPSATPSDV
121  PTTPFASAKP DSSVTASSEL TSSTNDVSTE LSSESQKQPE VPQEAVPTPK AAETTEVEPK
181  TDISEDSTSA NRPVPNESAS EEVSSAAPAQ APAEKEETSA PAAQKAVADT TSVATSNGLS
241  YAPNHAYNPM NAGLQPQTAA FKEEVASAFG ITSFSGYRPG DPGDHGKGLA IDFMVPENSA
301  LGDQVAQYAI DHMAERGISY VIWKQRFYAP FASIYGPAYT WNPMPDRGSI TENHYDHVHV
361  SFNA* (SEQ ID NO:10)
```

Figure 11

```
   1 CAAGAGTGGA CACCACGATC GGTTACAGAA ATCAAGTCTG AACTCGTCCT AGTTGATAAT
  61 GTTTTTACTT ATATAGTAAA ATACGGTGAC ACTTTAAGCA CAATTGCTGA AGCAATGGGG
 121 ATTGATGTGC ATGTCTTAGG AGATATTAAT CATATTGCTA ATATTGACTT AATTTTTCCA
 181 GACACGATCC TAACAGCAAA CTACAACCAA CACGGTCAGG CAACGACTTT GACGGTTCAA
 241 GCACCTGCTT CTAGTCCATC TAGCGTTAGT CATGTACCTA GCAGTGAGCC ATTACCCCAA
 301 GCATCTGCCA CCTCTCAACC GACTGTTCCT ATGGCACCAT CTGCGACACC ATCTGATGTC
 361 CCAACGACAC CATTCGCATC TGCAAAGCCA GATAGTTCTG TGACAGCGTC ATCTGAGCTC
 421 ACATCGTCAA CGAATGATGT TTCGACTGAG TTGTCTAGCG AATCACAAAA GCAGCCAGAA
 481 GTACCACAAG AAGCAGTTCC AACTCCTAAA GCAGCTGAAC CGACTGAAGT CGAACCTAAG
 541 ACAGACATCT CAGAAGACCC AACTTCAGCT AATAGGCCTG ACCTAACGA GAGTGCTTCA
 601 GAAGAAGCTT CTTCTGCGGC CCCAGCACAA GCTCCAGCAG AAAAAGAAGA AACCTCTCAG
 661 ATGTTAACTG CGCCAGCAGC ACAAAAAGCT GTAGCTGACA CCACAAGTGT TGCAACCTCA
 721 AACGGCCTTT CTTACGCTCC AAACCATGCC TACAATCCAA TGAATGCAGG GCTTCAACCA
 781 CAAACAGCAG CCTTCAAAGA AGAAGTGGCT TCTGCCTTTG GTATTACGTC ATTTAGTGGT
 841 TACCGTCCAG GAGATCCAGG AGATCATGGT AAAGGATTAG CCATTGACTT TATGGTACCG
 901 GTTAGCTCTA CGCTTGGTGA TCAAGTTGCT CAATATGCCA TTGACCATAT GGCAGAGCGT
 961 GGTATTTCAT ACGTTATTTG GAAACAGCGA TTCTATGCGC CATTTGCAAG TATTTACGGA
1021 CCAGCCTACA CATGGAACCC CATGCCAGAT CGCGGCAGTA TTACAGAAAA CCATTATGAT
1081 CATGTTCATG TCTCCTTTAA TGCTTAA (SEQ ID NO:11)
```

Figure 12

```
   1 QEWTPRSVTE IKSELVLVDN VFTYIVKYGD TLSTIAEAMG IDVHVLGDIN HIANIDLIFP
  61 DTILTANYNQ HGQATTLTVQ APASSPSSVS HVPSSEPLPQ ASATSQPTVP MAPSATPSDV
 121 PTTPFASAKP DSSVTASSEL TSSTNDVSTE LSSESQKQPE VPQEAVPTPK AAEPTEVEPK
 181 TDISEDPTSA NRPVPNESAS EEASSAAPAQ APAEKEETSQ MLTAPAAQKA VADTTSVATS
 241 NGLSYAPNHA YNPMNAGLQP QTAAFKEEVA SAFGITSFSG YRPGDPGDHG KGLAIDFMVP
 301 VSSTLGDQVA QYAIDHMAER GISYVIWKQR FYAPFASIYG PAYTWNPMPD RGSITENHYD
 361 HVHVSFNA* (SEQ ID NO:12)
```

Figure 13

```
1     CAAGAGTGGA CACCACGATC GGTTACAGAA ATCAAGTCTG AACTCGTCCT AGTTGATAAT
61    GTTTTTACTT ATACTGTAAA ATACGGTGAC ACTTTAAGCA CAATTGCTGA AGCAATGGGG
121   ATTGATGTGC ATGTCTTAGG AGATATTAAT CATATTGCTA ATATTGACCT AATTTTTCCA
181   GACACGATCC TAACAGCAAA CTACAATCAA CACGGTCAGG CAACGAATTT GACGGTTCAA
241   GCACCTGCTT CTAGTCCAGC TAGCGTTAGT CATGTACCTA GCAGTGAGCC ATTACCCCAA
301   GCATCTGCCA CCTCTCAACC GACTGTTCCT ATGGCACCAC CTGCGACACC ATCTGATGTC
361   CCAACGACAC CATTCGCATC TGCAAAGCCA GATAGTTCTG TGACAGCGTC ATCTGAGCTC
421   ACATCGTCAA CGAATGATGT TTCGACTGAG TTGTCTAGCG AATCACAAAA GCAGCCAGAA
481   GTACCACAAG AAGCAGTTCC AACTCCTAAA GCAGCTGAAA CGACTGAAGT CGAACCTAAG
541   ACAGACATCT CAGAAGCCCC AACTTCAGCT AATAGGCCTG TACCTAACGA GAGTGCTTCA
601   GAAGAAGTTT CTTCTGCGGC CCCAGCACAA GCCCCAGCAG AAAAAGAAGA AACCTCTGCG
661   CCAGCAGCAC AAAAAGCTGT AGCTGACACC ACAAGTGTTG CAACCTCAAA TGGCCTTTCT
721   TACGCTCCAA ACCATGCCTA CAATCCAATG AATGCAGGGC TTCAACCACA AACAGCAGCC
781   TTCAAAGAAG AAGTGGCTTC TGCCTTTGGT ATTACGTCAT TTAGTGGTTA CCGTCCAGGT
841   GATCCAGGAG ATCATGGTAA AGGTTTGGCC ATTGATTTTA TGGTGCCTGA AAATTCTGCT
901   CTTGGTGATC AAGTTGCTCA ATATGCCATT GACCATATGG CAGAGCGTGG TATTTCATAC
961   GTTATTTGGA AACAGCGATT CTATGCGCCA TTTGCAAGTA TTTACGGACC AGCCTACACA
1021  TGGAACCCCA TGCCAGATCG CGGCAGTATT ACAGAAAACC ATTATGATCA TGTTCATGTC
1081  TCCTTTAATG CTTAA (SEQ ID NO:13)
```

Figure 14

```
1     QEWTPRSVTE IKSELVLVDN VFTYTVKYGD TLSTIAEAMG IDVHVLGDIN HIANIDLIFP
61    DTILTANYNQ HGQATNLTVQ APASSPASVS HVPSSEPLPQ ASATSQPTVP MAPPATPSDV
121   PTTPFASAKP DSSVTASSEL TSSTNDVSTE LSSESQKQPE VPQEAVPTPK AAETTEVEPK
181   TDISEAPTSA NRPVPNESAS EEVSSAAPAQ APAEKEETSA PAAQKAVADT TSVATSNGLS
241   YAPNHAYNPM NAGLQPQTAA FKEEVASAFG ITSFSGYRPG DPGDHGKGLA IDFMVPENSA
301   LGDQVAQYAI DHMAERGISY VIWKQRFYAP FASIYGPAYT WNPMPDRGSI TENHYDHVHV
361   SFNA* (SEQ ID NO:14)
```

Figure 15

```
  1  CAAGAGTGGA CACCACGATC GGTTACAGAA ATCAAGTCTG AACTCGTCCT AGTTGATAAT
 61  GTTTTTACTT ATACAGTAAA ATACGGTGAC ACTTTAAGCA CAATTGCTGA AGCAATGGGG
121  ATTGATGTGC ATGTCTTAGG AGATATTAAT CATATTGCTA ATATTGACTT AATTTTTCCA
181  GACACGATCC TAACAGCAAA CTACAATCAA CACGGTCAGG CAACGACTTT GACGGTTCAA
241  GCACCTGCTT CTAGTCCAGC TAGCGTTAGT CATGTACCTA GCAGTGAGCC ATTACCCCAA
301  GCATCTGCCA CCTCTCAACC GACTGTTCCT ATGGCACCAT CTGCGACACC ATTAGCATCT
361  GCAAAGCCAG ATAGTTCTGT GACAGCGTCA TCTGAGCTCA CATCGTCAAC GAATGATGTT
421  TCGACTGAGT CGTCTAGCGA ATCACAAAAG CAGCCAGAAG TACCACAAGA AGCAGTTCCA
481  ACTCCTAAAG CAGCTGAAAC GACTGAAGTC GAACCTAAGA CAGACATCTC AGAAGACCCA
541  ACTTCAGCTA ATAGGCCTGT ACCTAACGAG AGTGCTTCAG AAGAAGTTTC TTCTGCGGCC
601  CCAGCACAAG CCCCAGCAGA AAAAGAAGAA ACCTCTGCGC AGCAGCACA AAAAGCTGTA
661  GCTGACACCA CAAGTGTTGC AACCTCAAAC GGCCTTTCTT ACGCTCCAAA CCATGCCTAC
721  AATCCAATGA ATGCAGGGCT TCAACCACAA ACAGCAGCCT TCAAAGAAGA AGTGGCTTCT
781  GCCTTTGGTA TTACGTCATT TAGTGGTTAC CGTCCAGGTG ACCCAGGAGA TCATGGTAAA
841  GGTTTGGCCA TTGATTTTAT GGTGCCTGAA AATTCTGCTC TTGGTGATCA AGTTGCTCAA
901  TATGCCATTG ACCATATGGC AGAGCGTGGT ATTTCATACG TTATTTGGAA ACAGCGATTC
961  TATGCGCCAT TTGCAAGTAT TTACGGACCA GCTTACACAT GGAACCCCAT GCCAGATCGC
1021 GGCAGTATTA CAGAAAACCA TTATGATCAT GTTCATGTCT CCTTTAATGC TTAA (SEQ ID
NO:15)
```

Figure 16

```
  1  QEWTPRSVTE IKSELVLVDN VFTYTVKYGD TLSTIAEAMG IDVHVLGDIN HIANIDLIFP
 61  DTILTANYNQ HGQATTLTVQ APASSPASVS HVPSSEPLPQ ASATSQPTVP MAPSATPLAS
121  AKPDSSVTAS SELTSSTNDV STESSSESQK QPEVPQEAVP TPKAAETTEV EPKTDISEDP
181  TSANRPVPNE SASEEVSSAA PAQAPAEKEE TSAPAAQKAV ADTTSVATSN GLSYAPNHAY
241  NPMNAGLQPQ TAAFKEEVAS AFGITSFSGY RPGDPGDHGK GLAIDFMVPE NSALGDQVAQ
301  YAIDHMAERG ISYVIWKQRF YAPFASIYGP AYTWNPMPDR GSITENHYDH VHVSFNA*
(SEQ ID NO:16)
```

Figure 17A

```
12384     1 ATGATTATTACTAAAAAGAGCTTATTTGTGACAAGTGTCGCTTTGTCGTT  50
2699      1 ATGATTATTACTAAAAAGAGCTTATTTGTGACAAGTGTCGCTTTGTCGTT  50
B514      1 ATGATTATTACTAAAAAGAGCTTATTTGTGACAAGTGTCGCTTTGTCGTT  50
Spy57     1 ATGATTATTACTAAAAAGAGCTTATTTGTGACAAGTGTCGCTTTGTCGTT  50
U09352    1 ATGATTATTACTAAAAAGAGTTTATTTGTGACAAGTGTCGCTTTGTCGTT  50
Oklahoma  1 ATGATTATTACTAAAAAGAGCTTATTTGTGACAAGTGTCGCTTTGTCGTT  50
            ******************** *****************************

12384    51 AGCACCTTTGGCGACAGCACAGGCACAAGAGTGGACACCACGATCGGTTA 100
2699     51 AGCACCTTTGGCGACAGCGCAGGCACAAGAGTGGACACCACGATCGGTTA 100
B514     51 AGCACCTTTGGCGACAGCGCAGGCACAAGAGTGGACACCACGATCGGTTA 100
Spy57    51 AGTACCTTTGGCGACAGCGCAGGCACAAGAGTGGACACCACGATCGGTTA 100
U09352   51 AGCACCTTTGGCGACAGCGCAGGCACAAGAGTGGACACCACGATCGGTTA 100
Oklahoma 51 AGTACCTTTGGCGACAGCGCAGGCACAAGAGTGGACACCACGATCGGTTA 100
            ** ************** ********************************

12384   101 CAGAAATCAAGTCTGAACTCGTCCTAGTTGATAATGTTTTTACTTATACT 150
2699    101 CAGAAATCAAGTCTGAACTCGTCCTAGTTGATAATGTTTTTACTTATATA 150
B514    101 CAGAAATCAAGTCTGAACTCGTCCTAGTTGATAATGTTTTTACTTATACA 150
Spy57   101 CAGAAATCAAGTCTGAACTCGTCCTAGTTGATAATGTTTTTACTTATACT 150
U09352  101 CACAAATCAAGTCTGAACTCGTCCTAGTTGATAATGTTTTTACTTATACA 150
Oklahoma 101 CAGAAATCAAGTCTGAACTCGTCCTAGTTGATAATGTTTTTACTTATACT 150
            ** **********************************************

12384   151 GTAAAATACGGTGACACTTTAAGCACAATTGCTGAAGCAATGGGAATTGA 200
2699    151 GTAAAATACGGTGACACTTTAAGCACAATTGCTGAAGCAATGGGGATTGA 200
B514    151 GTAAAATACGGTGACACTTTAAGCACAATTGCTGAAGCAATGGGGATTGA 200
Spy57   151 GTAAAATACGGTGACACTTTAAGCACAATTGCTGAAGCAATGGGGATTGA 200
U09352  151 GTAAAATACGGTGACACTTTAAGCACAATTGCTGAAGCAATGGGGATTGA 200
Oklahoma 151 GTAAAATACGGTGACACTTTAAGCACAATTGCTGAAGCAATGGGGATTGA 200
            ********************************************* ****

12384   201 TGTGCATGTCTTAGGAGATATTAATCATATTGCTAATATTGACTTAATTT 250
2699    201 TGTGCATGTCTTAGGAGATATTAATCATATTGCTAATATTGACTTAATTT 250
B514    201 TGTGCATGTCTTAGGAGATATTAATCATATTGCTAATATTGACTTAATTT 250
Spy57   201 TGTGCATGTCTTAGGAGATATTAATCATATTGCTAATATTGACCTAATTT 250
U09352  201 TGTGCATGTCTTAGGAGATATTAATCATATTGCTAATATTGACTTAATTT 250
Oklahoma 201 TGTGCATGTCTTAGGAGATATTAATCATATTGCTAATATTGACCTAATTT 250
            ******************************************* *****

12384   251 TTCCAGACACGATCCTAACAGCCAACTACAACCAACACGGTCAGGCAACG 300
2699    251 TTCCAGACACGATCCTAACAGCAAACTACAACCAACACGGTCAGGCAACG 300
B514    251 TTCCAGACACGATCCTAACAGCAAACTACAATCAACACGGTCAGGCAACG 300
Spy57   251 TTCCAGACACGATCCTAACAGCAAACTACAATCAACACGGTCAGGCAACG 300
U09352  251 TTCCAGACACGATCCTAACAGCAAACTACAACCAACACGGTCAGGCAACG 300
Oklahoma 251 TTCCAGACACGATCCTAACAGCAAACTACAATCAACACGGTCAGGCAACG 300
            ********************** ******* *******************

12384   301 ACTTTGACGGTTCAAGCGCCTGCTTCTAGTCCAGCTAGCGTTAGTCATGT 350
2699    301 ACTTTGACGGTTCAAGCACCTGCTTCTAGTCCATCTAGCGTTAGTCATGT 350
B514    301 ACTTTGACGGTTCAAGCACCTGCTTCTAGTCCAGCTAGCGTTAGTCATGT 350
Spy57   301 AATTTGACGGTTCAAGCACCTGCTTCTAGTCCAGCTAGCGTTAGTCATGT 350
U09352  301 ACTTTGACGGTTCAAGCGCCTGCTTCTAGTCCAGCTAGCGTTAGTCATGT 350
Oklahoma 301 AATTTGACGGTTCAAGCACCTGCTTCTAGTCCAGCTAGCGTTAGTCATGT 350
            * ************** **************** ****************
```

Figure 17B

```
12384      739  GCAGCACAAAAAGCTGTAGCTGACACCACAAGTGTTGCAACCTCAAATGG   788
2699       751  GCAGCACAAAAAGCTGTAGCTGACACCACAAGTGTTGCAACCTCAAACGG   800
B514       718  GCAGCACAAAAAGCTGTAGCTGACACCACAAGTGTTGCAACCTCAAACGG   767
Spy57      739  GCAGCACAAAAAGCTGTAGCTGACACCACAAGTGTTGCAACCTCAAATGG   788
U09352     751  GCAGCACAAAAAGCTGTAGCTGACACCACAAGTGTTGCAACCTCAAACGG   800
Oklahoma   739  GCAGCACAAAAAGCTGTAGCTGACACCACAAGTGTTGCAACCTCAAATGG   788
                ************************************************ **

12384      789  CCTTTCTTACGCTCCAAACCATGCCTACAATCCAATGAATGCAGGGCTTC   838
2699       801  CCTTTCTTACGCTCCAAACCATGCCTACAATCCAATGAATGCAGGGCTTC   850
B514       768  CCTTTCTTACGCTCCAAACCATGCCTACAATCCAATGAATGCAGGGCTTC   817
Spy57      789  CCTTTCTTACGCTCCAAACCATGCCTACAATCCAATGAATGCAGGGCTTC   838
U09352     801  CCTTTCTTACGCTCCAAACCATGCCTACAATCCAATGAATGCAGGGCTTC   850
Oklahoma   789  CCTTTCTTACGCTCCAAACCATGCCTACAATCCAATGAATGCAGGGCTTC   838
                **************************************************

12384      839  AACCACAAACAGCAGCCTTCAAAGAAGAAGTGGCTTCTGCCTTTGGTATT   888
2699       851  AACCACAAACAGCAGCCTTCAAAGAAGAAGTGGCTTCTGCCTTTGGTATT   900
B514       818  AACCACAAACAGCAGCCTTCAAAGAAGAAGTGGCTTCTGCCTTTGGTATT   867
Spy57      839  AACCACAAACAGCAGCCTTCAAAGAAGAAGTGGCTTCTGCCTTTGGTATT   888
U09352     851  AACCACAAACAGCAGCCTTCAAAGAAGAAGTG-CTTCTGCCTTTGGTATT   899
Oklahoma   839  AACCACAAACAGCAGCCTTCAAAGAAGAAGTGGCTTCTGCCTTTGGTATT   888
                ******************************** *****************

12384      889  ACGTCATTTAGTGGTTACCGTCCAGGTGATCCAGGAGATCAT-GGTAAAG   937
2699       901  ACGTCATTTAGTGGTTACCGTCCAGGTGATCCAGGAGATCAT-GGTAAAG   949
B514       868  ACGTCATTTAGTGGTTACCGTCCAGGTGACCCAGGAGATCAT-GGTAAAG   916
Spy57      889  ACGTCATTTAGTGGTTACCGTCCAGGTGATCCAGGAGATCAT-GGTAAAG   937
U09352     900  ACGTCATTTAGTGGTTACCGTCCAGGTGATCCAGGAGATCATTGGTAAAG   949
Oklahoma   889  ACGTCATTTAGTGGTTACCGTCCAGGTGATCCAGGAGATCAT-GGTAAAG   937
                **************************** ************* *******

12384      938  GTTTGGCCATTGATTTTATGGTGCCTGAAAATTCTGCTCTTGGTGATCAA   987
2699       950  GATTAGCCATTGACTTTATGGTACCGGTTAGCTCTACGCTTGGTGATCAA   999
B514       917  GTTTGGCCATTGATTTTATGGTGCCTGAAAATTCTGCTCTTGGTGATCAA   966
Spy57      938  GTTTGGCCATTGATTTTATGGTGCCTGAAAATTCTGCTCTTGGTGATCAA   987
U09352     950  GATTAGCCATTGACTTTATGGTACCGGTTAGCTCTACGCTTGGTGATCAA   999
Oklahoma   938  GTTTGGCCATTGATTTTATGGTGCCTGAAAATTCTGCTCTTGGTGATCAA   987
                *  ** ******** ******** **  *    *** * ***********

12384      988  GTTGCTCAATATGCCATTGACCATATGGCAGAGCGTGGTATTTCATACGT  1037
2699      1000  GTTGCTCAATATGCCATTGACCATATGGCAGAGCGTGGTATTTCATACGT  1049
B514       967  GTTGCTCAATATGCCATTGACCATATGGCAGAGCGTGGTATTTCATACGT  1016
Spy57      988  GTTGCTCAATATGCCATTGACCATATGGCAGAGCGTGGTATTTCATACGT  1037
U09352    1000  GTTGCTCAATATGCCATTGACCATATGGCAGACGTGGTATTTCATACGT  1049
Oklahoma   988  GTTGCTCAATATGCCATTGACCATATGGCAGAGCGTGGTATTTCATACGT  1037
                ******************************** *****************

12384     1038  TATTTGGAAACAGCGATTCTATGCGCCATTTGCAAGTATTTACGGACCAG  1087
2699      1050  TATTTGGAAACAGCGATTCTATGCGCCATTTGCAAGTATTTACGGACCAG  1099
B514      1017  TATTTGGAAACAGCGATTCTATGCGCCATTTGCAAGTATTTACGGACCAG  1066
Spy57     1038  TATTTGGAAACAGCGATTCTATGCGCCATTTGCAAGTATTTACGGACCAG  1087
U09352    1050  TATTTGGAAACAGCGATTCTATGCGCCATTTGCAAGTATTTACGGACCAG  1099
Oklahoma  1038  TATTTGGAAACAGCGATTCTATGCGCCATTTGCAAGTATTTACGGACCAG  1087
                **************************************************
```

Figure 17C

```
12384      1088 CCTACACATGGAACCCCATGCCAGATCGCGGCAGTATTACAGAAAACCAT 1137
2699       1100 CCTACACATGGAACCCCATGCCAGATCGCGGCAGTATTACAGAAAACCAT 1149
B514       1067 CTTACACATGGAACCCCATGCCAGATCGCGGCAGTATTACAGAAAACCAT 1116
Spy57      1088 CCTACACATGGAACCCCATGCCAGATCGCGGCAGTATTACAGAAAACCAT 1137
U09352     1100 CCTACACATGGAACCCCATGCCAGATCGCGGCAGTATTACAGTTTTCCAT 1149
Oklahoma   1088 CCTACACATGGAACCCCATGCCAGATCGCGGCAGTATTACAGAAAACCAT 1137
                *  ******************************************  ****

12384      1138 TATGATCATGTTCATGTCTCCTTTAATGCTTAA 1170
2699       1150 TATGATCATGTTCATGTCTCCTTTAATGCTTAA 1182
B514       1117 TATGATCATGTTCATGTCTCCTTTAATGCTTAA 1149
Spy57      1138 TATGATCATGTTCATGTCTCCTTTAATGCTTAA 1170
U09352     1150 TATGATCATGTTCATGTCTCCTTTAATGCTTAA 1182
Oklahoma   1138 TATGATCATGTTCATGTCTCCTTTAATGCTTAA 1170
                *********************************
```

Figure 18A

```
12384      1  MIITKKSLFVTSVALSLAPLATAQAQEWTPRSVTEIKSELVLVDNVFTYT  50
2699       1  MIITKKSLFVTSVALSLAPLATAQAQEWTPRSVTEIKSELVLVDNVFTYI  50
B514       1  MIITKKSLFVTSVALSLAPLATAQAQEWTPRSVTEIKSELVLVDNVFTYT  50
Spy57      1  MIITKKSLFVTSVALSLVPLATAQAQEWTPRSVTEIKSELVLVDNVFTYT  50
U09352     1  MIITKKSLFVTSVALSLAPLATAQAQEWTPRSVTQIKSELVLVDNVFTYT  50
Oklahoma   1  MIITKKSLFVTSVALSLVPLATAQAQEWTPRSVTEIKSELVLVDNVFTYT  50
              ******************.****************.**************

12384     51  VKYGDTLSTIAEAMGIDVHVLGDINHIANIDLIFPDTILTANYNQHGQAT 100
2699      51  VKYGDTLSTIAEAMGIDVHVLGDINHIANIDLIFPDTILTANYNQHGQAT 100
B514      51  VKYGDTLSTIAEAMGIDVHVLGDINHIANIDLIFPDTILTANYNQHGQAT 100
Spy57     51  VKYGDTLSTIAEAMGIDVHVLGDINHIANIDLIFPDTILTANYNQHGQAT 100
U09352    51  VKYGDTLSTIAEAMGIDVHVLGDINHIANIDLIFPDTILTANYNQHGQAT 100
Oklahoma  51  VKYGDTLSTIAEAMGIDVHVLGDINHIANIDLIFPDTILTANYNQHGQAT 100
              **************************************************

12384    101  TLTVQAPASSPASVSHVPSSEPLPQASATSQSTVPMAPSATPSDVPTTPF 150
2699     101  TLTVQAPASSPSSVSHVPSSEPLPQASATSQPTVPMAPSATPSDVPTTPF 150
B514     101  TLTVQAPASSPASVSHVPSSEPLPQASATSQPTVPMAPSATP-------L 143
Spy57    101  NLTVQAPASSPASVSHVPSSEPLPQASATSQPTVPMAPPATPSDVPTTPF 150
U09352   101  TLTVQAPASSPASVSHVPSSEPLPQASATSQSTIPMAPSATPSDVPTTPL 150
Oklahoma 101  NLTVQAPASSPASVSHVPSSEPLPQASATSQPTVPMAPPATPSDVPTTPF 150
              .*********.******************* * **** ***

12384    151  ASAKPDSSVTASSELTSSTNDVSTELSSESQKQPEVPQEAVPTPKAAETT 200
2699     151  ASAKPDSSVTASSELTSSTNDVSTELSSESQKQPEVPQEAVPTPKAAEPT 200
B514     144  ASAKPDSSVTASSELTSSTNDVSTESSSESQKQPEVPQEAVPTPKAAETT 193
Spy57    151  ASAKPDSSVTASSELTSSTNDVSTELSSESQKQPEVPQEAVPTPKAAETT 200
U09352   151  ASAKPDSFVTASSELTSSTNDVSTELSSESQKQPEVPQEAEPTPKAAEST 200
Oklahoma 151  ASAKPDSSVTASSELTSSTNDVSTELSSESQKQPEVPQEAVPTPKAAETT 200
              ******* ***************** *************** ****** *

12384    201  EVEPKTDISEDSTSANRPVPNESASEEVSSAAPAQAPAEKE----ETSAP 246
2699     201  EVEPKTDISEDPTSANRPVPNESASEEASSAAPAQAPAEKEETSQMLTAP 250
B514     194  EVEPKTDISEDPTSANRPVPNESASEEVSSAAPAQAPAEKE----ETSAP 239
Spy57    201  EVEPKTDISEAPTSANRPVPNESASEEVSSAAPAQAPAEKE----ETSAP 246
U09352   201  EVEPKTDISEDSTSANRPVPNGSASEEASSAAPAQAPAEKEETSQMLTAP 250
Oklahoma 201  EVEPKTDISEAPTSANRPVPNESASEEVSSAAPAQAPAEKE----ETSAP 246
              **********  ********* ***** **************      **

12384    247  AAQKAVADTTSVATSNGLSYAPNHAYNPMNAGLQPQTAAFKEEVASAFGI 296
2699     251  AAQKAVADTTSVATSNGLSYAPNHAYNPMNAGLQPQTAAFKEEVASAFGI 300
B514     240  AAQKAVADTTSVATSNGLSYAPNHAYNPMNAGLQPQTAAFKEEVASAFGI 289
Spy57    247  AAQKAVADTTSVATSNGLSYAPNHAYNPMNAGLQPQTAAFKEEVASAFGI 296
U09352   251  AAQKAVADTTSVATSNGLSYAPNHAYNPMNAGLQPQTAAFKEEVLLPLVL 300
Oklahoma 247  AAQKAVADTTSVATSNGLSYAPNHAYNPMNAGLQPQTAAFKEEVASAFGI 296
              ********************************************

12384    297  TSFSGYRPGDPGDHGKGLAIDFMVPENSALGDQVAQYAIDHMAERGISYV 346
2699     301  TSFSGYRPGDPGDHGKGLAIDFMVPVSSTLGDQVAQYAIDHMAERGISYV 350
B514     290  TSFSGYRPGDPGDHGKGLAIDFMVPENSALGDQVAQYAIDHMAERGISYV 339
Spy57    297  TSFSGYRPGDPGDHGKGLAIDFMVPENSALGDQVAQYAIDHMAERGISYV 346
U09352   301  RHLVVTVQEIQEIIGKGLAIDFMVPVSSTLGDQVAQYAIDHMADGGISYV 350
Oklahoma 297  TSFSGYRPGDPGDHGKGLAIDFMVPENSALGDQVAQYAIDHMAERGISYV 346
                       **********  *.**********.  *****
```

Figure 18B

```
12384    347 IWKQRFYAPFASIYGPAYTWNPMPDRGSITENHYDHVHVSFNA 389
2699     351 IWKQRFYAPFASIYGPAYTWNPMPDRGSITENHYDHVHVSFNA 393
B514     340 IWKQRFYAPFASIYGPAYTWNPMPDRGSITENHYDHVHVSFNA 382
Spy57    347 IWKQRFYAPFASIYGPAYTWNPMPDRGSITENHYDHVHVSFNA 389
U09352   351 IWKQRFYAPFASIYGPAYTWNPMPDRGSITVFHYDHVHVSFNA 393
Oklahoma 347 IWKQRFYAPFASIYGPAYTWNPMPDRGSITENHYDHVHVSFNA 389
             ***************************  **********
```

Figure 19

```
   1 ATGAAGAAAA GAATGTTATT AGCGTCAACA GTAGCCTTGT CATTTGCCCC
  51 AGTATTGGCA ACTCAAGCAG AAGAAGTTCT TTGGACTGCA CGTAGTGTTG
 101 AGCAAATCCA AAACGATTTG ACTAAAACGG ACAACAAAAC AAGTTATACC
 151 GTACAGTATG GTGATACTTT GAGCACCATT GCAGAAGCCT TGGGTGTAGA
 201 TGTCACAGTG CTTGCGAATC TGAACAAAAT CACTAATATG GACTTGATTT
 251 TCCCAGAAAC TGTTTTGACA ACGACTGTCA ATGAAGCAGA AGAAGTAACA
 301 GAAGTTGAAA TCCAAACACC TCAAGCAGAC TCTAGTGAAG AAGTGACAAC
 351 TGCGACAGCA GATTTGACCA CTAATCAAGT GACCGTTGAT GATCAAACTG
 401 TTCAGGTTGC AGACCTTTCT CAACCAATTG CAGAAGTTAC AAAGACAGTG
 451 ATTGCTTCTG AAGAAGTGGC ACCATCTACG GGCACTTCTG TCCCAGAGGA
 501 GCAAACGACC GAAACAACTC GCCCAGTTGA AGAAGCAACT CCTCAGGAAA
 551 CGACTCCAGC TGAGAAGCAG GAAACACAAG CAAGCCCTCA AGCTGCATCA
 601 GCAGTGGAAG TAACTACAAC AAGTTCAGAA GCAAAAGAAG TAGCATCATC
 651 AAATGGAGCT ACAGCAGCAG TTTCTACTTA TCAACCAGAA GAGACGAAAA
 701 TAATTTCAAC AACTTACGAG GCTCCAGCTG CGCCCGATTA TGCTGGACTT
 751 GCAGTAGCAA AATCTGAAAA TGCAGGTCTT CAACCACAAA CAGCTGCCTT
 801 TAAAGAAGAA ATTGCTAACT TGTTTGGCAT TACATCCTTT AGTGGTTATC
 851 GTCCAGGAGA CAGTGGAGAT CACGGAAAAG GTTTGGCTAT CGACTTTATG
 901 GTACCAGAAC GTTCAGAATT AGGGGATAAG ATTGCGAAT ATGCTATTCA
 951 AAATATGGCC AGCCGTGGCA TTAGTTACAT CATCTGGAAA CAACGTTTCT
1001 ATGCTCCATT CGATAGCAAA TATGGGCCAG CTAACACTTG GAACCCAATG
1051 CCAGACCGTG GTAGTGTGAC AGAAAATCAC TATGATCACG TTCACGTTTC
1101 AATGAATGGA TAA (SEQ ID NO:17)
```

Figure 20

```
   1 MKKRMLLAST VALSFAPVLA TQAEEVLWTA RSVEQIQNDL TKTDNKTSYT
  51 VQYGDTLSTI AEALGVDVTV LANLNKITNM DLIFPETVLT TTVNEAEEVT
 101 EVEIQTPQAD SSEEVTTATA DLTTNQVTVD DQTVQVADLS QPIAEVTKTV
 151 IASEEVAPST GTSVPEEQTT ETTRPVEEAT PQETTPAEKQ ETQASPQAAS
 201 AVEVTTTSSE AKEVASSNGA TAAVSTYQPE ETKIISTTYE APAAPDYAGL
 251 AVAKSENAGL QPQTAAFKEE IANLFGITSF SGYRPGDSGD HGKGLAIDFM
 301 VPERSELGDK IAEYAIQNMA SRGISYIIWK QRFYAPFDSK YGPANTWNPM
 351 PDRGSVTENH YDHVHVSMNG * (SEQ ID NO:18)
```

STREPTOCOCCUS PYOGENES ANTIGENS

CROSS-REFERENCES TO RELATED APPLICATIONS

This application is a continuation of U.S. patent application Ser. No. 10/332,231, now issued as U.S. Pat. No. 7,247,308 on Jul. 24, 2007, which has a filing date of Apr. 22, 2003, and which is a national stage application filed under 35 U.S.C. §371 of International Patent Application No. PCT/CA01/01001, accorded an international filing date of Jul. 6, 2001, which claims the benefit of U.S. Provisional Patent Application No. 60/216,465, filed Jul. 6, 2000, all of which applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 484112_419D1—SEQUENCE_LISTING.txt. The text file is 62 KB, was created on Jul. 9, 2007, and is being submitted electronically via EFS-Web, concurrent with the filing of the specification.

FIELD OF THE INVENTION

The present invention is related to antigens, more particularly a polypeptide antigen of *Streptococcus pyogenes* (also called group A *Streptococcus* (GAS)) bacterial pathogen which may be useful for prophylaxis, diagnostic and/or therapy of streptococcal infection.

BACKGROUND OF THE INVENTION

*Streptococci* are gram (+) bacteria which are differentiated by group specific carbohydrate antigens A through O which are found at the cell surface. *Streptococcus pyogenes* isolates are further distinguished by type-specific M protein antigens. M proteins are important virulence factors which are highly variable both in molecular weights and in sequences. Indeed, more than 80-M protein types have been identified on the basis of antigenic differences.

*Streptococcus pyogenes* is responsible for many diverse infection types, including pharyngitis, erysipelas and impetigo, scarlet fever, and invasive diseases such as bacteremia and necrotizing fasciitis and also toxic shock. A resurgence of invasive disease in recent years has been documented in many countries, including those in North America and Europe. Although the organism is sensitive to antibiotics, the high attack rate and rapid onset of sepsis results in high morbidity and mortality.

To develop a vaccine that will protect individuals from *Streptococcus pyogenes* infection, efforts have concentrated on virulence factors such as the type-specific M proteins. However, the amino-terminal portion of M proteins was found to induce cross-reactive antibodies which reacted with human myocardium, tropomyosin, myosin, and vimentin, which might be implicated in autoimmune diseases. Others have used recombinant techniques to produce complex hybrid proteins containing amino-terminal peptides of M proteins from different serotypes. However, a safe vaccine containing all *Streptococcus pyogenes* serotypes will be highly complex to produce and standardize.

In addition to the serotype-specific antigens, other *Streptococcus pyogenes* proteins have generated interest as potential vaccine candidates. The C5a peptidase, which is expressed by at least *Streptococcus pyogenes* 40 serotypes, was shown to be immunogenic in mice, but its capacity to reduce the level of nasopharyngeal colonization was limited. Other investigators have also focused on the streptococcal pyrogenic exotoxins which appear to play an important role in pathogenesis of infection. Immunization with these proteins prevented the deadly symptoms of toxic shock, but did not prevent colonization.

Therefore there remains an unmet need for *Streptococcus pyogenes* antigens that may be used vaccine components for prophylaxis, diagnostic and/or therapy of *Streptococcus* infection.

SUMMARY OF THE INVENTION

According to one aspect, the present invention provides an isolated polynucleotide encoding a polypeptide having at least 70% identity to a second polypeptide comprising a sequence chosen from SEQ ID NOs: 2, 4, 6, 8, 10, 12, 14, 16, 20 or fragments, analogues or derivatives thereof.

According to one aspect, the present invention provides an isolated polynucleotide encoding a polypeptide having at least 95% identity to a second polypeptide comprising a sequence chosen from SEQ ID NOs: 2, 4, 6, 8, 10, 12, 14, 16, 20 or fragments, analogues or derivatives thereof.

In other aspects, there are provided novel polypeptides encoded by polynucleotides of the invention, vectors comprising polynucleotides of the invention operably linked to an expression control region, as well as host cells transfected with said vectors, pharmaceutical or vaccine compositions and methods of producing polypeptides comprising culturing said host cells under conditions suitable for expression.

BRIEF DESCRIPTION OF THE DRAWINGS

FIG. 1 is the DNA sequence of BVH-P1 gene from serotype 3 *S. pyogenes* strain ATCC 12384 with a secretion signal at position 1 to 75; SEQ ID NO: 1.

FIG. 2 is the amino acid sequence BVH-P1 protein from serotype 3 *S. pyogenes* strain ATCC12384 with a secretion signal at position 1 to 25; SEQ ID NO:2.

FIG. 3 is the DNA sequence of BVH-P1 gene from *S. pyogenes* strain LSPQ2699 (ATCC19615) with a secretion signal at position 1 to 75; SEQ ID NO:3.

FIG. 4 is the amino acid sequence BVH-P1 protein from *S. pyogenes* strain LSPQ2699 (ATCC 19615) with a secretion signal at position 1 to 25; SEQ ID NO:4.

FIG. 5 is the DNA sequence of BVH-P1 gene from *S. pyogenes* strain SPY57 with a secretion signal at position 1 to 75; SEQ ID NO:5.

FIG. 6 is the amino acid sequence BVH-P1 protein from *S. pyogenes* strain SPY57 with a secretion signal at position 1 to 25; SEQ ID NO:6.

FIG. 7 is the DNA sequence of BVH-P1 gene from *S. pyogenes* strain B514 with a secretion signal at position 1 to 75; SEQ ID NO:7.

FIG. 8 is the amino acid sequence BVH-P1 protein from *S. pyogenes* strain B514 with a secretion signal at position 1 to 25; SEQ ID NO:8.

FIG. 9 is the DNA sequence BVH-P1 gene without a secretion signal from serotype 3 *S. pyogenes* strain ATCC12384; SEQ ID NO:9.

FIG. 10 is the amino acid sequence BVH-P1 protein without a secretion signal from serotype 3 *S. pyogenes* strain ATCC12384; SEQ ID NO:10.

FIG. 11 is the DNA sequence BVH-P1 gene without a secretion signal from serotype 3 *S. pyogenes* strain LSPQ2699 (ATCC19615); SEQ ID NO:11.

FIG. 12 is the amino acid sequence BVH-P1 protein without a secretion signal from serotype 3 *S. pyogenes* strain LSPQ2699 (ATCC19615); SEQ ID NO:12.

FIG. 13 is the DNA sequence BVH-P1 gene without a secretion signal from serotype 3 *S. pyogenes* strain SPY57; SEQ ID NO:13.

FIG. 14 is the amino acid sequence BVH-P1 protein without a secretion signal from serotype 3 *S. pyogenes* strain SPY57; SEQ ID NO:14.

FIG. 15 is the DNA sequence BVH-P1 gene without a secretion signal from serotype 3 *S. pyogenes* strain B514; SEQ ID NO:15.

FIG. 16 is the amino acid sequence BVH-P1 protein without a secretion signal from serotype 3 *S. pyogenes* strain B514; SEQ ID NO:16.

FIG. 17A-C depicts the comparison of the nucleotide sequences of the BVH-P1 genes from ATCC12384 (SEQ ID NO:1), LSPQ2699 (ATCC19615) (SEQ ID NO:3), SPY57 (SEQ ID NO:5), B514 (SEQ ID NO:7), ATCC 70029 (Oklahoma) (SEQ ID NO:32), and T28/51/4 (U09352) (SEQ ID NO:30) *S. pyogenes* strains by using the program Clustal W from MacVector sequence analysis software (version 6.5). Underneath the alignment, there is a consensus line. Shaded nucleotides are identical between every sequences and gaps in the sequence introduced by alignment are indicated by hyphens.

FIG. 18A-B depicts the comparison of the predicted amino acid sequences of the BVH-P1 open reading frames from ATCC12384 (SEQ ID NO:2), LSPQ2699 (ATCC19615) (SEQ ID NO:4), SPY57 (SEQ ID NO:6), B514 (SEQ ID NO:8), ATCC 70029 (Oklahoma) (SEQ ID NO:33) and T28/51/4 (U09352) (SEQ ID NO:31) *S. pyogenes* strains by using the program Clustal W from MacVector sequence analysis software (version 6.5). Underneath the alignment, there is a consensus line. Shaded amino acid residues are identical between every sequences and gaps in the sequence introduced by alignment are indicated by hyphens.

FIG. 19 is the DNA sequence of a gene from *S. pneumonia*; SEQ ID NO:17.

FIG. 20 is the amino acid sequence of a protein from *S. pneumonia*; SEQ ID NO:18.

DETAILED DESCRIPTION OF THE INVENTION

According to one aspect, the present invention provides an isolated polynucleotide encoding a polypeptide having at least 70% identity to a second polypeptide comprising a sequence chosen from SEQ ID NOs: 2, 4, 6, 8, 10, 12, 14, 16, 20 or fragments, analogues or derivatives thereof.

According to one aspect, the present invention provides an isolated polynucleotide encoding a polypeptide having at least 95% identity to a second polypeptide comprising a sequence chosen from SEQ ID NOs: 2, 4, 6, 8, 10, 12, 14, 16, 20 or fragments, analogues or derivatives thereof.

According to one aspect, the present invention relates to polypeptides characterized by the amino acid sequence comprising SEQ ID NOs: 2, 4, 6, 8, 10, 12, 14, 16, 20 or fragments, analogues or derivatives thereof.

According to one aspect, the present invention provides an isolated polynucleotide encoding a polypeptide capable of generating antibodies having binding specificity for a polypeptide comprising a sequence chosen from SEQ ID NOs: 2, 4, 6, 8, 10, 12, 14, 16, 20 or fragments, analogues or derivatives thereof.

In accordance with the present invention, there is provided a consensus nucleotide sequence depicted in FIG. 17. As can be seen by the alignement, the polynucleotide encoding the polypeptide of the invention is well conserved. Without restricting the scope of the invention, the following table 1 shows the possible modifications. SEQ ID NO:19 covers the consensus nucleotide sequence depicted in FIG. 17 with the modifications illustrated in Table 1:

| Position on alignment in FIG. 17 | Possible nucleotide |
|---|---|
| 21 | C or T |
| 53 | C or T |
| 69 | G or A |
| 103 | G or C |
| 149 | C or T |
| 150 | A or T |
| 195 | G or A |
| 244 | T or C |
| 273 | A or C |
| 282 | T or C |
| 302 | C or A |
| 318 | A or G |
| 334 | G or T |
| 394 | C or T |
| 400 | G or A |
| 415 | C or T |
| 428-448 | [CTGATGTCCCAACGACACCAT] (SEQ ID NO:34) or none |
| 450 | C or A |
| 473 | C or T |
| 501 | G or A |
| 527 | T or C |
| 572 | T or A |
| 573 | T or A |
| 595 | A or C |
| 596 | C or G |
| 597 | G or C |
| 630 | A or G |
| 632 | A or C |
| 633 | C or T |
| 634 | C or T |
| 665 | A or G |

-continued

| Position on alignment in FIG. 17 | Possible nucleotide |
|---|---|
| 666 | G or A |
| 683 | T or C |
| 708 | C or T |
| 733 | [CAGATGTTAACT] (SEQ ID NO:35) or none |
| 798 | T or C |
| 883 | G or none |
| 927 | T or A |
| 930 | T or C |
| 943 | T or none |
| 952 | T or A |
| 955 | G or A |
| 964 | T or C |
| 973 | G or A |
| 976 | T or G |
| 978 | A or T |
| 979 | A or T |
| 981 | A or G |
| 982 | T or C |
| 986 | G or A |
| 988 | T or G |
| 1033 | G or C |
| 1034 | C or G |
| 1102 | C or T |
| 1143 | A or T |
| 1144 | A or T |
| 1145 | A or T |
| 1146 | A or T |

In accordance with the present invention, there is provided a consensus amino acid sequence depicted in FIG. 18. As can be seen by the alignment, the polypeptide of the invention is well conserved. Without restricting the scope of the invention, the following table 2 shows the possible modifications. SEQ ID NO:20 covers the consensus nucleotide sequence depicted in FIG. 18 with the modifications illustrated in Table 2:

| Position on alignment in FIG. 18 | Possible amino acid |
|---|---|
| 18 | A or V |
| 35 | E or Q |
| 50 | T or I |
| 101 | T or N |
| 112 | A or S |
| 132 | P or S |
| 134 | V or I |
| 139 | S or P |
| 143 to 149 | SDVPTTP (SEQ ID NO:36) or none |
| 150 | F or L |
| 158 | S or F |
| 176 | L or S |
| 191 | V or E |
| 199 | T or P or S |
| 211 | D or A |
| 212 | P or S |
| 222 | E or G |
| 228 | V or A |
| 242 to 245 | ETSQ (SEQ ID NO:37) or none |
| 246 | E or M |
| 247 | T or L |
| 248 | S or T |
| 295 | A or L |
| 296 | S or L |
| 297 | A or P |
| 298 | F or L |
| 299 | G or V |
| 300 | I or L |
| 301 | T or R |
| 302 | S or H |
| 303 | F or L |
| 304 | S or V |
| 305 | G or V |
| 306 | Y or T |
| 307 | R or V |
| 308 | P or Q |
| 309 | G or E |
| 310 | D or I |
| 311 | P or Q |

-continued

| Position on alignment in FIG. 18 | Possible amino acid |
|---|---|
| 312 | G or E |
| 313 | D or I |
| 314 | H or I |
| 326 | E or V |
| 327 | N or S |
| 329 | A or T |
| 344 | E or D |
| 345 | R or G |
| 381 | E or V |
| 382 | N or F |

In accordance with the present invention, all polynucleotides encoding polypeptides are within the scope of the present invention.

In a further embodiment, the polypeptides in accordance with the present invention are antigenic.

In a further embodiment, the polypeptides in accordance with the present invention are immunogenic.

In a further embodiment, the polypeptides in accordance with the present invention can elicit an immune response in an individual.

In a further embodiment, the present invention also relates to polypeptides which are able to raise antibodies having binding specificity to the polypeptides of the present invention as defined above.

An antibody that "has binding specificity" is an antibody that recognizes and binds the selected polypeptide but which does not substantially recognize and bind other molecules in a sample, e.g., a biological sample. Specific binding can be measured using an ELISA assay in which the selected polypeptide is used as an antigen.

In accordance with the present invention, "protection" in the biological studies is defined by a significant increase in the survival curve, rate or period. Statistical analysis using the Log rank test to compare survival curves, and Fisher exact test to compare survival rates and numbers of days to death, respectively, might be useful to calculate P values and determine whether the difference between the two groups is statistically significant. P values of 0.05 are regarded as not significant.

As used herein, "fragments", "analogues" or "derivatives" of the polypeptides of the invention include those polypeptides in which one or more of the amino acid residues are substituted with a conserved or non-conserved amino acid residue (preferably conserved) and which may be natural or unnatural. In one embodiment, derivatives and analogues of polypeptides of the invention will have about 70% identity with those sequences illustrated in the figures or fragments thereof. That is, 70% of the residues are the same. In a further embodiment, polypeptides will have greater than 75% homology. In a further embodiment, polypeptides will have greater than 80% homology. In a further embodiment, polypeptides will have greater than 85% homology. In a further embodiment, polypeptides will have greater than 90% homology. In a further embodiment, polypeptides will have greater than 95% homology. In a further embodiment, polypeptides will have greater than 99% homology. In a further embodiment, derivatives and analogues of polypeptides of the invention will have less than about 20 amino acid residue substitutions, modifications or deletions and more preferably less than 10. Preferred substitutions are those known in the art as conserved i.e., the substituted residues share physical or chemical properties such as hydrophobicity, size, charge or functional groups.

The skilled person will appreciate that fragments, analogues or derivatives of the proteins or polypeptides of the invention will also find use in the context of the present invention, i.e., as antigenic/immunogenic material. Thus, for instance proteins or polypeptides which include one or more additions, deletions, substitutions or the like are encompassed by the present invention. In addition, it may be possible to replace one amino acid with another of similar "type," for instance, by replacing one hydrophobic amino acid with another hydrophobic amino acid.

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

In an alternative approach, the analogues or derivatives could be fusion proteins, incorporating moieties which render purification easier, for example by effectively tagging the desired protein or polypeptide, it may be necessary to remove the "tag" or it may be the case that the fusion protein itself retains sufficient antigenicity to be useful.

In an additional aspect of the invention there are provided antigenic/immunogenic fragments of the proteins or polypeptides of the invention, or of analogues or derivatives thereof.

The fragments of the present invention should include one or more epitopic regions or be sufficiently similar to such regions to retain their antigenic/immunogenic properties. Thus, for fragments according to the present invention the degree of identity is perhaps irrelevant, since they may be 100% identical to a particular part of a protein or polypeptide, homologue or derivative as described herein. The key issue, once again, is that the fragment retains the antigenic/immunogenic properties.

Thus, what is important for analogues, derivatives and fragments is that they possess at least a degree of the antigenicity/immunogenicity of the protein or polypeptide from which they are derived.

Also included are polypeptides which have fused thereto other compounds which alter the polypeptides biological or pharmacological properties i.e., polyethylene glycol (PEG) to increase half-life; leader or secretory amino acid sequences for ease of purification; prepro- and pro-sequences; and (poly)saccharides.

Furthermore, in those situations where amino acid regions are found to be polymorphic, it may be desirable to vary one or more particular amino acids to more effectively mimic the different epitopes of the different *streptococcus* strains.

Moreover, the polypeptides of the present invention can be modified by terminal —NH$_2$ acylation (e.g., by acetylation, or thioglycolic acid amidation, terminal carboxy amidation, e.g., with ammonia or methylamine) to provide stability, increased hydrophobicity for linking or binding to a support or other molecule.

Also contemplated are hetero and homo polypeptide multimers of the polypeptide fragments, analogues and derivatives. These polymeric forms include, for example, one or more polypeptides that have been cross-linked with cross-linkers such as avidin/biotin, gluteraldehyde or dimethylsuperimidate. Such polymeric forms also include polypeptides containing two or more tandem or inverted contiguous sequences, produced from multicistronic mRNAs generated by recombinant DNA technology.

Preferably, a fragment, analog or derivative of a polypeptide of the invention will comprise at least one antigenic region i.e., at least one epitope.

In order to achieve the formation of antigenic polymers (i.e., synthetic multimers), polypeptides may be utilized having bishaloacetyl groups, nitroarylhalides, or the like, where the reagents being specific for thio groups. Therefore, the link between two mercapto groups of the different peptides may be a single bond or may be composed of a linking group of at least two, typically at least four, and not more than 16, but usually not more than about 14 carbon atoms.

In a particular embodiment, polypeptide fragments, analogues and derivatives of the invention do not contain a methionine (Met) starting residue. Preferably, polypeptides will not incorporate a leader or secretory sequence (signal sequence). The signal portion of a polypeptide of the invention may be determined according to established molecular biological techniques. In general, the polypeptide of interest may be isolated from a streptococcal culture and subsequently sequenced to determine the initial residue of the mature protein and therefore the sequence of the mature polypeptide.

According to another aspect, there are provided vaccine compositions comprising one or more streptococcal polypeptides of the invention in admixture with a pharmaceutically acceptable carrier diluent or adjuvant. Suitable adjuvants include oils i.e., Freund's complete or incomplete adjuvant; salts i.e., $AlK(SO_4)_2$, $AlNa(SO_4)_2$, $AlNH_4(SO_4)_2$, silica, kaolin, carbon polynucleotides i.e., poly IC and poly AU. Preferred adjuvants include QuilA and Alhydrogel®. Vaccines of the invention may be administered parenterally by injection, rapid infusion, nasopharyngeal absorption, dermoabsorption, or bucal or oral. Pharmaceutically acceptable carriers also include tetanus toxoid.

The term vaccine is also meant to include antibodies. In accordance with the present invention, there is also provided the use of one or more antibodies having binding specificity for the polypeptides of the present invention for the treatment or prophylaxis of *streptococcus* infection and/or diseases and symptoms mediated by *streptococcus* infection.

Vaccine compositions of the invention are used for the treatment or prophylaxis of streptococcal infection and/or diseases and symptoms mediated by streptococcal infection As described in P. R. Murray (ed., in chief), E. J. Baron, M. A. Pfaller, F. C. Tenover and R. H. Yolken. Manual of Clinical Microbiology, ASM Press, Washington, D.C. sixth edition, 1995, 1482p, which are herein incorporated by reference. In one embodiment, vaccine compositions of the present invention are used for the prophylaxis or treatment of pharyngitis, erysipelas and impetigo, scarlet fever, and invasive diseases such as bacteremia and necrotizing fasciitis and also toxic shock. In one embodiment, vaccine compositions of the invention are used for the prophylaxis or treatment of *Streptococcus* infection and/or diseases and symptoms mediated by *Streptococcus* infection, in particular group A *Streptococcus* (pyogenes), group B *Streptococcus* (GBS or agalactiae), *S. pneumoniae*, dysgalactiae, uberis, *nocardia* as well as *Staphylococcus aureus*. In a further embodiment, the *Streptococcus* infection is *Streptococcus pyogenes*.

In a particular embodiment, vaccines are administered to those individuals at risk of *streptococcus* infection such as infants, elderly and immunocompromised individuals.

As used in the present application, the term "individuals" include mammals. In a further embodiment, the mammal is human.

Vaccine compositions are preferably in unit dosage form of about 0.001 to 100 µg/kg (antigen/body weight) and more preferably 0.01 to 10 µg/kg and most preferably 0.1 to 1 µg/kg 1 to 3 times with an interval of about 1 to 6 week intervals between immunizations.

Vaccine compositions are preferably in unit dosage form of about 0.1 µg to 10 mg and more preferably 1 µg to 1 mg and most preferably 10 to 100 µg 1 to 3 times with an interval of about 1 to 6 week intervals between immunizations.

According to another aspect, there are provided polynucleotides encoding polypeptides characterized by the amino acid sequence chosen from SEQ ID NOs: 2, 4, 6, 8, 10, 12, 14, 16, 20 or fragments, analogues or derivatives thereof.

In one embodiment, polynucleotides are those illustrated in SEQ ID NOs: 1, 3, 5, 7, 9, 11, 13, 15, 19 which may include the open reading frames (ORF), encoding polypeptides of the invention.

It will be appreciated that the polynucleotide sequences illustrated in the figures may be altered with degenerate codons yet still encode the polypeptides of the invention. Accordingly the present invention further provides polynucleotides which hybridize to the polynucleotide sequences herein above described (or the complement sequences thereof) having 50% identity between sequences. In one embodiment, at least 70% identity between sequences. In one embodiment, at least 75% identity between sequences. In one embodiment, at least 80% identity between sequences. In one embodiment, at least 85% identity between sequences. In one embodiment, at least 90% identity between sequences. In a further embodiment, polynucleotides are hybridizable under stringent conditions i.e., having at least 95% identity. In a further embodiment, more than 97% identity.

Suitable stringent conditions for hybridization can be readily determined by one of skilled in the art (see for example Sambrook et al., (1989) Molecular cloning: A Laboratory Manual, $2^{nd}$ ed., Cold Spring Harbor, N.Y.; Current Protocols in Molecular Biology, (1999) Edited by Ausubel F. M. et al., John Wiley & Sons, Inc., N.Y.).

In a further embodiment, the present invention provides polynucleotides that hybridise under stringent conditions to either (a) a DNA sequence encoding a polypeptide or (b) the complement of a DNA sequence encoding a polypeptide;

wherein said polypeptide comprising a sequence chosen from SEQ ID NOs: 2, 4, 6, 8, 10, 12, 14, 16, 20 or fragments or analogues thereof.

In a further embodiment, the present invention provides polynucleotides that hybridise under stringent conditions to either (a) a DNA sequence encoding a polypeptide or (b) the complement of a DNA sequence encoding a polypeptide;

wherein said polypeptide comprises at least 10 contiguous amino acid residues from a polypeptide comprising a sequence chosen from SEQ ID NOs: 2, 4, 6, 8, 10, 12, 14, 16, 20 or fragments or analogues thereof.

In a further embodiment, polynucleotides are those encoding polypeptides of the invention illustrated in SEQ ID NOs: 2, 4, 6, 8, 10, 12, 14, 16, 20.

In a further embodiment, polynucleotides are those illustrated in SEQ ID NOs: 1, 3, 5, 7, 9, 11, 13, 15, 19 encoding polypeptides of the invention.

As will be readily appreciated by one skilled in the art, polynucleotides include both DNA and RNA.

The present invention also includes polynucleotides complementary to the polynucleotides described in the present application.

In a further aspect, polynucleotides encoding polypeptides of the invention, or fragments, analogues or derivatives thereof, may be used in a DNA immunization method. That is, they can be incorporated into a vector which is replicable and expressible upon injection thereby producing the antigenic polypeptide in vivo. For example polynucleotides may be incorporated into a plasmid vector under the control of the CMV promoter which is functional in eukaryotic cells. Preferably the vector is injected intramuscularly.

According to another aspect, there is provided a process for producing polypeptides of the invention by recombinant techniques by expressing a polynucleotide encoding said polypeptide in a host cell and recovering the expressed polypeptide product. Alternatively, the polypeptides can be produced according to established synthetic chemical techniques i.e., solution phase or solid phase synthesis of oligopeptides which are ligated to produce the full polypeptide (block ligation).

General methods for obtention and evaluation of polynucleotides and polypeptides are described in the following references: Sambrook et al, Molecular Cloning: A Laboratory Manual, 2nd ed., Cold Spring Harbor, N.Y., 1989; Current Protocols in Molecular Biology, edited by Ausubel F. M. et al., John Wiley and Sons, Inc. New York; PCR Cloning Protocols, from Molecular Cloning to Genetic Engineering, Edited by White B. A., Humana Press, Totowa, N.J., 1997, 490 pages; Protein Purification, Principles and Practices, Scopes R. K., Springer-Verlag, New York, 3rd Edition, 1993, 380 pages; Current Protocols in Immunology, edited by Coligan J. E. et al., John Wiley & Sons Inc., New York, which are herein incorporated by reference.

For recombinant production, host cells are transfected with vectors which encode the polypeptide, and then cultured in a nutrient media modified as appropriate for activating promoters, selecting transformants or amplifying the genes. Suitable vectors are those that are viable and replicable in the chosen host and include chromosomal, non-chromosomal and synthetic DNA sequences e.g., bacterial plasmids, phage DNA, baculovirus, yeast plasmids, vectors derived from combinations of plasmids and phage DNA. The polypeptide sequence may be incorporated in the vector at the appropriate site using restriction enzymes such that it is operably linked to an expression control region comprising a promoter, ribosome binding site (consensus region or Shine-Dalgamo sequence), and optionally an operator (control element). One can select individual components of the expression control region that are appropriate for a given host and vector according to established molecular biology principles (Sambrook et al., Molecular Cloning: A Laboratory Manual, 2nd ed., Cold Spring Harbor, N.Y., 1989; Current Protocols in Molecular Biology, edited by Ausubel F. M. et al., John Wiley and Sons, Inc., New York, incorporated herein by reference). Suitable promoters include but are not limited to LTR or SV40 promoter, E. coli lac, tac or trp promoters and the phage lambda PL promoter. Vectors will preferably incorporate an origin of replication as well as selection markers i.e., ampicilin resistance gene. Suitable bacterial vectors include pET, pQE70, pQE60, pQE-9, pbs, pD10 phagescript, psiX174, pbluescript SK, pbsks, pNH8A, pNH16a, pNH18A, pNH46A, ptrc99a, pKK223-3, pKK233-3, pDR540, pRIT5 and eukaryotic vectors pBlueBacIII, pWLNEO, pSV2CAT, pOG44, pXT1, pSG, pSVK3, pBPV, pMSG and pSVL. Host cells may be bacterial i.e., E. coli, Bacillus subtilis, Streptomyces; fungal i.e., Aspergillus niger, Aspergillus nidulins; yeast i.e., Saccharomyces or eukaryotic i.e., CHO, COS.

Upon expression of the polypeptide in culture, cells are typically harvested by centrifugation then disrupted by physical or chemical means (if the expressed polypeptide is not secreted into the media) and the resulting crude extract retained to isolate the polypeptide of interest. Purification of the polypeptide from culture media or lysate may be achieved by established techniques depending on the properties of the polypeptide i.e., using ammonium sulfate or ethanol precipitation, acid extraction, anion or cation exchange chromatography, phosphocellulose chromatography, hydrophobic interaction chromatography, hydroxylapatite chromatography and lectin chromatography. Final purification may be achieved using HPLC.

The polypeptide may be expressed with or without a leader or secretion sequence. In the former case the leader may be removed using post-translational processing (see U.S. Pat. No. 4,431,739; U.S. Pat. No. 4,425,437; and U.S. Pat. No. 4,338,397 incorporated herein by reference) or be chemically removed subsequent to purifying the expressed polypeptide.

According to a further aspect, the streptococcal polypeptides of the invention may be used in a diagnostic test for Streptococcus infection, in particular Streptococcus pyogenes infection. Several diagnostic methods are possible, for example detecting Streptococcus organism in a biological sample, the following procedure may be followed:

a) obtaining a biological sample from an individual;

b) incubating an antibody or fragment thereof reactive with a Streptococcus polypeptide of the invention with the biological sample to form a mixture; and c) detecting specifically bound antibody or bound fragment in the mixture which indicates the presence of Streptococcus.

Alternatively, a method for the detection of antibody specific to a Streptococcus antigen in a biological sample containing or suspected of containing said antibody may be performed as follows:

a) obtaining a biological sample from an individual;

b) incubating one or more streptococcus polypeptides of the invention or fragments thereof with the biological sample to form a mixture; and c) detecting specifically bound antigen or bound fragment in the mixture which indicates the presence of antibody specific to Streptococcus.

One of skill in the art will recognize that this diagnostic test may take several forms, including an immunological test such as an enzyme-linked immunosorbent assay (ELISA), a radio-immunoassay or a latex agglutination assay, essentially to determine whether antibodies specific for the protein are present in an individual.

The DNA sequences encoding polypeptides of the invention may also be used to design DNA probes for use in detecting the presence of Streptococcus in a biological sample suspected of containing such bacteria. The detection method of this invention comprises:

a) obtaining the biological sample from an individual;
b) incubating one or more DNA probes having a DNA sequence encoding a polypeptide of the invention or fragments thereof with the biological sample to form a mixture; and
c) detecting specifically bound DNA probe in the mixture which indicates the presence of *Streptococcus* bacteria.

The DNA probes of this invention may also be used for detecting circulating *Streptococcus* i.e., *Streptococcus pyogenes* nucleic acids in a sample, for example using a polymerase chain reaction, as a method of diagnosing *Streptococcus* infections. The probe may be synthesized using conventional techniques and may be immobilized on a solid phase, or may be labeled with a detectable label. A preferred DNA probe for this application is an oligomer having a sequence complementary to at least about 6 contiguous nucleotides of the *Streptococcus pyogenes* polypeptides of the invention.

Another diagnostic method for the detection of *Streptococcus* in an individual comprises:
a) labeling an antibody reactive with a polypeptide of the invention or fragment thereof with a detectable label;
b) administering the labeled antibody or labeled fragment to the patient; and
c) detecting specifically bound labeled antibody or labeled fragment in the patient which indicates the presence of *Streptococcus*.

A further aspect of the invention is the use of the *Streptococcus* polypeptides of the invention as immunogens for the production of specific antibodies for the diagnosis and in particular the treatment of *Streptococcus* infection. Suitable antibodies may be determined using appropriate screening methods, for example by measuring the ability of a particular antibody to passively protect against *Streptococcus* infection in a test model. One example of an animal model is the mouse model described in the examples herein. The antibody may be a whole antibody or an antigen-binding fragment thereof and may belong to any immunoglobulin class. The antibody or fragment may be of animal origin, specifically of mammalian origin and more specifically of murine, rat or human origin. It may be a natural antibody or a fragment thereof, or if desired, a recombinant antibody or antibody fragment. The term recombinant antibody or antibody fragment means antibody or antibody fragment which was produced using molecular biology techniques. The antibody or antibody fragments may be polyclonal, or preferably monoclonal. It may be specific for a number of epitopes associated with the *Streptococcus pyogenes* polypeptides but is preferably specific for one.

A further aspect of the invention is the use of the antibodies directed to the *streptococcus* polypeptides of the invention for passive immunization. One could use the antibodies described in the present application. Suitable antibodies may be determined using appropriate screening methods, for example by measuring the ability of a particular antibody to passively protect against *streptococcus* infection in a test model. One example of an animal model is the mouse model described in the examples herein. The antibody may be a whole antibody or an antigen-binding fragment thereof and may belong to any immunoglobulin class. The antibody or fragment may be of animal origin, specifically of mammalian origin and more specifically of murine, rat or human origin. It may be a natural antibody or a fragment thereof, or if desired, a recombinant antibody or antibody fragment. The term recombinant antibody or antibody fragment means antibody or antibody fragment which was produced using molecular biology techniques. The antibody or antibody fragments may be polyclonal, or preferably monoclonal. It may be specific for a number of epitopes associated with the *Streptococcus pneumoniae* polypeptides but is preferably specific for one.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLE 1

This example illustrates the cloning of *S. pyogenes* gene.

The coding region of *S. pyogenes* gene BVH-P1 (SEQ ID NO:1) was amplified by PCR (DNA Thermal Cycler Gene-Amp® PCR system 2400 Perkin Elmer, San Jose, Calif.) from genomic DNA of serotype 3 *S. pyogenes* strain ATCC12384 using the following oligos that contained base extensions for the addition of restriction sites NcoI (CCATGG) and XhoI (CTCGAG): DMAR16 (5'-CAGGC-CATGGAGTGGACACCACGATCGGTTAC-3') (SEQ ID NO:21); DMAR17 (5'-GCCGCTCGAGAGCATTAAAG-GAGACATGAACATGATC-3') (SEQ ID NO:22). PCR products were purified from agarose gel using a QIA®quick gel extraction kit from QIA®gen following the manufacturer's instructions (Chatsworth, Calif.), and digested with NcoI and XhoI (Pharmacia Canada Inc, Baie d'Urfé, Canada). The pET-21d(+) vector (Novagen®, Madison, Wis.) was digested with NcoI and XhoI and purified from agarose gel using a QIA®quick gel extraction kit from QIA®gen (Chatsworth, Calif.). The NcoI-XhoI PCR products were ligated to the NcoI-XhoI pET-21d(+)expression vector. The ligated products were transformed into *E. coli* strain DH5α [φ80dlacZΔM15 Δ(lacZYA-argF) U169 endA1 recA1 hsdR17($r_K$−$m_K$+) deoR thi-1 supE44 λ⁻gyrA96 relA1] (Gibco BRL, Gaithersburg, Md.) according to the method of Simanis (Hanahan, D. DNA Cloning, 1985, D. M. Glover (ed), pp. 109-135). Recombinant pET-21d(+)plasmid (rpET21d(+)) containing BVH-P1 gene was purified using a QIA®gen plasmid kit (Chatsworth, Calif.) and DNA insert was sequenced (Taq Dye Deoxy Terminator Cycle Sequencing kit, ABI, Foster City, Calif.).

It was determined that the open reading frame (ORF) which codes for BVH-P1 contains 1170-bp and encodes a 389 amino acid residues polypeptide with a predicted pI of 4.37 and a predicted molecular mass of 41054 Da.

Analysis of the predicted amino acid residues sequence (SEQ ID NO:2)using the Spscan software (Wisconsin Sequence Analysis Package; Genetics Computer Group) suggested the existence of a 25 amino acid residues signal peptide (MIITKKSLFVTSVALSLAPLATAQA) (SEQ ID NO:23), which ends with a cleavage site situated between an alanine and a glutamine residues. Analysis of this ORF did not reveal the presence of repetitive structures, cell wall anchoring motif (LPXTG) (SEQ ID NO:24), or IgA binding motif (MLKKIE) (SEQ ID NO:25).

An ORF which shares 62% with the *S. pyogenes* BVH-P1 gene was initially presented in the patent application PCT/CA99/00114 which described Group B *Streptococcus* antigens. BVH-P1 gene was also found to share homology (62% identity) with an ORF present in the genome of *S. pneumoniae* (The Institute for Genomic Research).

EXAMPLE 2

This example describes the PCR amplification and sequencing of BVH-P1 gene from other *S. pyogenes* strains and the evaluation of the level of molecular conservation of this gene.

Lancefield's serogroup A *S. pyogenes* LSPQ2296 (ATCC 19615) was provided by the laboratoire de la santé publique du Québec, Sainte-Anne-de-Bellevue; serotype 1 *S. pyogenes* SPY57 clinical isolate was provided by the centre de recherche en infectiologie du centre hospitalier de l'université Laval, Sainte-Foy; and *S. pyogenes* strain B514 which was initially isolated from a mouse was provided by Susan Hollingshead, from University of Alabama, Birmingham. The respective coding region of *S. pyogenes* gene BVH-P1 from strains ATCC 12384 (SEQ ID NO:1), LSPQ2699 (ATCC19615) (SEQ ID NO:3), SPY57 (SEQ ID NO:5), and B514 (SEQ ID NO:7) were amplified by PCR (DNA Thermal Cycler GeneAmp® PCR system 2400 Perkin Elmer, San Jose, Calif.) from bacterial cell lysates using the following oligos DMAR69 (5'-CTGGGAAGATTATCTAGCACAT-TAATAC-3') (SEQ ID NO:26); DMAR72 (5'-CATAACGT-TAAAACTGTCTAAAGGG-3') (SEQ ID NO:27). PCR products were purified from agarose gel using a QIAquick gel extraction kit from QIAgen following the manufacturer's instructions (Chatsworth, Calif.) and the DNA insert were sequenced (Taq Dye Deoxy Terminator Cycle Sequencing kit, ABI, Foster City, Calif.). The predicted amino acid sequences from strains ATCC12384 (SEQ ID NO:2), LSPQ2699 (ATCC19615) (SEQ ID NO:4), SPY57 (SEQ ID NO:6), and B514 (SEQ ID NO:8) were respectively presented in the following FIGS. 2, 4, 6, and 8.

The FIGS. 17 and 18 respectively depict the consensus nucleotide and predicted amino acid sequences established for *S. pyogenes* BVH-P1. In addition to the sequences presented herewith, the BVH-P1 gene sequences from the genome sequencing project at the University of Oklahoma (serotype M1 *S. pyogenes* strain ATCC 70029: see web site at dna1.chem.ou.edu/strep-.html) and from (Kil et al. 1994. *Infect. Immun.* 62:2440-2449: GenBank accession number U09352) were also included. No function or role in the pathogenesis of the bacteria or protection against infection was described by Kil et al. for the sequence with GenBank accession number U09352. This latter sequence presented by Kil et al. was shown to be located upstream of a *S. pyogenes* 67 kDa myosin-cross-reactive antigen.

Pairwise comparison of the BVH-P1 predicted protein sequences revealed between 95 to 100% identity with the exception of the BVH-P1 sequence obtained from GenBank under the accesssion number U09352. Pairwise comparison of that particular sequence with the other five BVH-P1 sequences indicated identity between 87 to 91%. This lower homology can be explained by the presence of two regions (119-124 and 262-281) which are more divergent comparatively to the other BVH-P1 gene sequences. Beside these two regions in the BVH-P1 sequence obtained from GenBank under the accesssion number U09352, the BVH-P1 genes showed great similarity in overall organization.

EXAMPLE 3

This example illustrates the cloning of *S. pyogenes* protein gene in CMV plasmid pCMV-GH.

The DNA coding region of a *S. pyogenes* protein was inserted in phase downstream of a human growth hormone (hGH) gene which was under the transcriptional control of the cytomegalovirus (CMV) promoter in the plasmid vector pCMV-GH (Tang et al., *Nature*, 1992, 356:152). The CMV promoter is a non functional plasmid in *E. coli* cells but is active upon administration of the plasmid in eukaryotic cells. The vector also incorporated the ampicillin resistance gene.

The coding region of BVH-P1 gene (SEQ ID NO:9) without its leader peptide region was amplified by PCR (DNA Thermal Cycler GeneAmp® PCR system 2400 Perkin Elmer, San Jose, Calif.) from genomic DNA of serotype 3 *S. pyogenes* strain ATCC12384 using the following oligos that contained base extensions for the addition of restriction sites BamHI (GGATCC) and SalI (GTCGAC): DMAR24 (5'-TACCCGGATCCCCAAGAGTGGACACCACGATCGG-3') (SEQ ID NO:28); DMAR25 (5'-GCGCTCGTC-GACGCGTATCTCAGCCTCTTATAGGGC-3') (SEQ ID NO:29). The PCR product was purified from agarose gel using a QIA®quick gel extraction kit from QIA®gen (Chatsworth, Calif.), digested with restriction enzymes (Pharmacia Canada Inc, Baie d'Urfe, Canada). The pCMV-GH vector (Laboratory of Dr. Stephen A. Johnston, Department of Biochemistry, The University of Texas, Dallas, Tex.) was digested with BamHI and SalI and purified from agarose gel using the QIA®quick gel extraction kit from QIA®gen (Chatsworth, Calif.). The BamHI-SalI DNA fragments were ligated to the BamHI-SalI pCMV-GH vector to create the hGH-BVH-P1 fusion protein under the control of the CMV promoter. The ligated products were transformed into *E. coli* strain DH5a [φ80dlacZΔM15 Δ(lacZYA-argF)U169 endA1 recA1 hsdR17($r_K^-$–$m_K^+$) deoR thi-1 supE44 λ⁻gyrA96 relA1] (Gibco BRL, Gaithersburg, Md.) according to the method of Simanis (Hanahan, D. DNA Cloning, 1985, D. M. Glover (ed), pp. 109-135). The recombinant pCMV plasmid was purified using a QIA®gen plasmid kit (Chatsworth, Calif.) and the nucleotide sequence of the DNA insert was verified by DNA sequencing.

EXAMPLE 4

This example illustrates the use of DNA to elicit an immune response to *S. pyogenes* antigens.

A group of 8 female BALB/c mice (Charles River, St-Constant, Québec, Canada) are immunized by intramuscular injection of 100 μl three times at two- or three-week intervals with 50 μg of recombinant pCMV-GH encoding BVH-P1 gene in presence of 50 μg of granulocyte-macrophage colony-stimulating factor (GM-CSF)-expressing plasmid pCMV-GH-GM-CSF (Laboratory of Dr. Stephen A. Johnston, Department of Biochemistry, The University of Texas, Dallas, Tex.). As control, a group of mice are injected with 50 μg of pCMV-GH in presence of 50 μg of pCMV-GH-GM-CSF. Blood samples are collected from the orbital sinus prior to each immunization and seven days following the third injection and serum antibody responses are determined by ELISA using purified BVH-P1-His•Tag from SEQ ID NO:11 *S. pyogenes* recombinant protein as coating antigen.

EXAMPLE 5

This example illustrates the production and purification of recombinant *S. pyogenes* BVH-P1 protein.

The recombinant pET-21d(+)plasmid with BVH-P1 gene corresponding to the SEQ ID NO:9 was used to transform by electroporation (Gene Pulser II apparatus, BIO-RAD Labs, Mississauga, Canada) *E. coli* strain BL21(DE3) (F⁻ompT hsdS$_B$ ($r^-_B m^-_B$) gal dcm (DE3)) (Novagen®, Madison, Wis.). In this strain of *E. coli*, the T7 promotor controlling expression of the recombinant protein is specifically recognized by the T7 RNA polymerase (present on the λDE3 prophage) whose gene is under the control of the lac promotor which is inducible by isopropyl-β-d-thio-galactopyranoside (IPTG). The transformant BL21(DE3)/rpET was grown at 37° C. with agitation at 250 rpm in LB broth (peptone 10 g/L, yeast extract 5 g/L, NaCl 10 g/L) containing 100 μg of carbenicillin (Sigma-Aldrich Canada Ltd., Oakville, Canada) per ml until the $A_{600}$ reached a value of 0.6. In order to induce the production of *S. pyogenes* BVH-P1-His•Tag recombinant protein (from SEQ ID NO:10), the cells were incubated for 3 additional hours in the presence of IPTG at a final concentration of 1 mM. Induced cells from a 500 ml culture were pelleted by centrifugation and frozen at −70° C.

The purification of the recombinant proteins from the soluble cytoplasmic fraction of IPTG-induced BL21(DE3)/rpET21b(+) was done by affinity chromatography based on the properties of the His•Tag sequence (6 consecutive histidine residues) to bind to divalent cations ($Ni^{2+}$) immobilized on the His•Bind metal chelation resin. Briefly, the pelleted cells obtained from a 500 mL culture induced with IPTG was resuspended in lysis buffer (20 mM Tris, 500 mM NaCl, 10 mM imidazole, pH 7.9) containing 1 mM PMSF, sonicated and centrifuged at 12,000×g for 20 min to remove debris. The supernatant was deposited on a Ni-NTA agarose column (QIA®gen, Mississauga, Ontario, Canada). The *S. pyogenes* BVH-P1-His•Tag recombinant protein (from SEQ ID NO:10) was eluted with 250 mM imidazole-500 mM NaCl-20 mM Tris pH 7.9. The removal of the salt and imidazole from the sample was done by dialysis against PBS at 4° C. The quantities of recombinant protein obtained from the soluble fraction of *E. coli* were estimated by MicroBCA (Pierce, Rockford, Ill.).

EXAMPLE 6

This example illustrates the accessibility to antibodies of the BVH-P1 protein at the surface of *S. pyogenes* strain.

Bacteria were grown in Todd Hewitt (TH) broth (Difco Laboratories, Detroit Mich.) with 0.5% Yeast extract (Difco Laboratories) and 0.5% peptone extract (Merck, Darmstadt, Germany) at 37° C. in a 8% $CO_2$ atmosphere to give an $OD_{490\ nm}$ of 0.600 (~$10^8$ CFU/ml). Dilutions of anti-BVH-P1 or control sera were then added and allowed to bind to the cells, which were incubated for 2 h at 4° C. Samples were washed 4 times in blocking buffer [phosphate-buffered saline (PBS) containing 2% bovine serum albumin (BSA)], and then 1 ml of goat fluorescein (FITC)-conjugated anti-mouse IgG+IgM diluted in blocking buffer was added. After an additional incubation of 60 min at room temperature, samples were washed 4 times in blocking buffer and fixed with 0.25% formaldehyde in PBS buffer for 18-24 h at 4° C. Cells were washed 2 times in PBS buffer and resuspended in 500 μl of PBS buffer. Cells were kept in the dark at 4° C. until analyzed by flow cytometry (Epics® XL; Beckman Coulter, Inc.). Flow cytometric analysis revealed that BVH-P1-specific antibodies efficiently recognized their corresponding surface exposed epitopes on both the homologous (ATCC12384; serotype3) and the heterologous (SPY57; serotype 1) *S. pyogenes* strains tested. It was determined that more than 90% of the 10,000 *S. pyogenes* cells analyzed were labeled with the antibodies present in the BVH-MC1 specific anti-sera. These observations clearly demonstrate that the BVH-P1 protein is accessible at the surface where it can be easily recognized by antibodies. Anti-*S. pyogenes* antibodies were shown to play an important role in the protection against *S. pyogenes* infection.

EXAMPLE 7

This example illustrates the protection against fatal *S. pyogenes* infection induced by passive immunization of mice with rabbit hyper-immune sera.

New Zealand rabbits (Charles River laboratories, Montreal, Canada) are injected subcutaneously at multiple sites with approximately 50 μg and 100 μg of BVH-P1-His•Tag protein (from SEQ ID NO:10) that was produced and purified as described in Example 5 and adsorbed to Alhydrogel® adjuvant (Superfos Biosector a/s). Rabbits are immunized three times at three-week intervals with the BVH-P1-His•Tag protein (from SEQ ID NO:10). Blood samples are collected three weeks after the third injection. The antibodies present in the serum are purified by precipitation using 40% saturated ammonium sulfate. Groups of 10 female CD-1 mice (Charles River) are injected intravenously with 500 μl of purified serum collected either from BVH-P1-His•Tag (from SEQ ID NO:10) immunized rabbits or rabbits immunized with an unrelated control recombinant protein. Eighteen hours later the mice are challenged with approximately $2\times10^7$ CFU of the type 3 *S. pyogenes* strain ATCC12384. Samples of the *S. pyogenes* challenge inoculum are plated on blood agar plates to determine the CFU and to verify the challenge dose. Deaths are recorded for a period of 5 days.

EXAMPLE 8

This example illustrates the protection of mice against fatal *S. pyogenes* infection induced by immunization with BVH-P1 protein.

Groups of 8 female CD-1 mice (Charles River) were immunized subcutaneously three times at three-week intervals with 20 μg of affinity purified *S. pyogenes* BVH-P1-His•Tag recombinant protein (from SEQ ID NO:10) in presence of 10 μg of QuilA adjuvant (Cedarlane Laboratories Ltd, Hornby, Canada) or, as control, with QuilA adjuvant alone in PBS. Blood samples were collected from the orbital sinus on day 1, 22 and 43 prior to each immunization and seven days (day 50) following the third injection. Analysis by ELISA using purified recombinant BVH-P1 protein (from SEQ ID NO:10) clearly indicated that this protein is highly immunogenic in animals. Indeed reciprocal ELISA titers higher than 106 were determined for the mice immunized with this recombinant protein. Two weeks later the mice were challenged with approximately $2\times10^7$ CFU of the type 3 *S. pyogenes* strain ATCC12384. Samples of the *S. pyogenes* challenge inoculum were plated on blood agar plates to determine the CFU and to verify the challenge dose. Deaths were recorded for a period of 5 days. Five out of the 8 (62%) mice immunized with three injections of 20 μg of purified recombinant BVH-P1 (from SEQ ID NO:10) and QuilA adjuvant survived the bacterial challenge to only 2/7 (28%) in the control group.

TABLE 3

Immunization of CD-1 mice with purified recombinant BVH-P1 protein confers protection against subsequent challenge with *S. pyogenes* strain ATCC 12384

| Groups | Survival of the mice challenged with *S. pyogenes* strain ATCC 12384 (Day after challenge: number of survivors/total number of mice challenged)) | | | | |
|---|---|---|---|---|---|
| | 1 | 2 | 3 | 4 | 5 |
| 20 μg of BVH-P1-His•Tag | 8/8 | 8/8 | 7/8 | 6/8 | 5/8 |
| Control | 7/7 | 6/7 | 3/7 | 2/7 | 2/7 |

The invention claimed is:

1. A method for eliciting an immune response against *Streptococcus pyogenes* in a host comprising administering to the host a composition that comprises (a) an isolated polypeptide comprising an immunogenic polypeptide fragment consisting of an amino acid sequence at least 90% identical to the amino acid sequence set forth in SEQ ID NO: 10, 12, 14, or 16; and (b) a pharmaceutically acceptable carrier or diluent.

2. The method according to claim 1 wherein the composition further comprises a pharmaceutically acceptable adjuvant.

3. A method for treating *Streptococcus pyogenes* infection in a host susceptible to *Streptococcus pyogenes* infection, said method comprising administering to the host a composition that comprises an isolated polypeptide comprising an immunogenic polypeptide fragment consisting of an amino acid sequence at least 90% identical to the amino acid sequence set forth in SEQ ID NO: 10, 12, 14, or 16;

and a pharmaceutically acceptable carrier or diluent.

4. The method according to claim 3 wherein the composition further comprises a pharmaceutically acceptable adjuvant.

5. A diagnostic method for detecting an antibody that specifically binds to a *Streptococcus pyogenes* antigen present in an individual comprising:
   (a) obtaining a biological sample from the individual;
   (b) incubating an isolated polypeptide comprising an immunogenic polypeptide fragment consisting of an amino acid sequence at least 90% identical to the amino acid sequence set forth in SEQ ID NO:10, 12, 14, or 16 with the biological sample to form a mixture; and
   (c) detecting specifically bound polypeptide in the mixture, which indicates the presence of the antibody that specifically binds to the *Streptococcus pyogenes* antigen.

6. A pharmaceutical composition comprising a polypeptide that comprises an immunogenic polypeptide fragment consisting of an amino acid sequence at least 90% identical to the amino acid sequence set forth in SEQ ID NO: 10, 12, 14, or 16 and a pharmaceutically acceptable carrier or diluent.

7. The pharmaceutical composition according to claim 6 further comprising a pharmaceutically acceptable adjuvant.

* * * * *

SEQUENCE LISTING

<160> NUMBER OF SEQ ID NOS: 37

<210> SEQ ID NO 1
<211> LENGTH: 1170
<212> TYPE: DNA
<213> ORGANISM: Streptococcus pyogenes

<400> SEQUENCE: 1

```
atgattatta ctaaaaagag cttatttgtg acaagtgtcg ctttgtcgtt agcacctttg      60
gcgacagcac aggcacaaga gtggacacca cgatcggtta cagaaatcaa gtctgaactc     120
gtcctagttg ataatgtttt tacttatact gtaaaatacg gtgacacttt aagcacaatt     180
gctgaagcaa tgggaattga tgtgcatgtc ttaggagata ttaatcatat tgctaatatt     240
gacttaattt ttccagacac gatcctaaca gccaactaca accaacacgg tcaggcaacg     300
actttgacgg ttcaagcgcc tgcttctagt ccagctagcg ttagtcatgt acctagcagt     360
gagccattac cccaagcatc tgccacctct caatcgactg ttcctatggc accatctgcg     420
acaccatctg atgtcccaac gacaccattc gcatctgcaa agccagatag ttctgtgaca     480
gcgtcatctg agctcacatc gtcaacgaat gatgtttcga ctgagttgtc tagcgaatca     540
caaaagcagc cagaagtacc acaagaagca gttccaactc ctaaagcagc tgaaacgact     600
gaagtcgaac taagacagac atctcagag gattcaactt cagctaatag gcctgtacct     660
aacgagagtg cttcagaaga gtttcttct gcggccccag cacaagcccc agcagaaaaa     720
gaagaaacct ctgcgccagc agcacaaaaa gctgtagctg acaccacaag tgttgcaacc     780
tcaaatggcc tttcttacgc tccaaaccat gcctacaatc caatgaatgc agggcttcaa     840
ccacaaacag cagccttcaa agaagaagtg gcttctgcct ttggtattac gtcatttagt     900
ggttaccgtc aggtgatcc aggagatcat ggtaaaggtt tggccattga tttatggtg      960
cctgaaaatt ctgctcttgg tgatcaagtt gctcaatatg ccattgacca tatggcagag    1020
cgtggtattt catacgttat ttggaaacag cgattctatg cgccatttgc aagtatttac    1080
ggaccagcct acacatggaa ccccatgcca gatcgcggca gtattacaga aaaccattat    1140
gatcatgttc atgtctcctt taatgcttaa                                     1170
```

<210> SEQ ID NO 2
<211> LENGTH: 389
<212> TYPE: PRT
<213> ORGANISM: Streptococcus pyogenes

<400> SEQUENCE: 2

Met Ile Ile Thr Lys Lys Ser Leu Phe Val Thr Ser Val Ala Leu Ser
  1               5                  10                  15

Leu Ala Pro Leu Ala Thr Ala Gln Ala Gln Glu Trp Thr Pro Arg Ser
              20                  25                  30

Val Thr Glu Ile Lys Ser Glu Leu Val Leu Val Asp Asn Val Phe Thr
          35                  40                  45

Tyr Thr Val Lys Tyr Gly Asp Thr Leu Ser Thr Ile Ala Glu Ala Met
      50                  55                  60

Gly Ile Asp Val His Val Leu Gly Asp Ile Asn His Ile Ala Asn Ile
 65                  70                  75                  80

Asp Leu Ile Phe Pro Asp Thr Ile Leu Thr Ala Asn Tyr Asn Gln His
              85                  90                  95

Gly Gln Ala Thr Thr Leu Thr Val Gln Ala Pro Ala Ser Ser Pro Ala

|       |       |       |       |       | 100   |       |       |       |       | 105   |       |       |       |       | 110   |       |       |
|-------|-------|-------|-------|-------|-------|-------|-------|-------|-------|-------|-------|-------|-------|-------|-------|-------|-------|

Ser Val Ser His Val Pro Ser Ser Glu Pro Leu Pro Gln Ala Ser Ala
    115                  120                  125

Thr Ser Gln Ser Thr Val Pro Met Ala Pro Ser Ala Thr Pro Ser Asp
130                135                  140

Val Pro Thr Thr Pro Phe Ala Ser Ala Lys Pro Asp Ser Ser Val Thr
145                150              155              160

Ala Ser Ser Glu Leu Thr Ser Ser Thr Asn Asp Val Ser Thr Glu Leu
            165              170              175

Ser Ser Glu Ser Gln Lys Gln Pro Glu Val Pro Gln Glu Ala Val Pro
        180                185              190

Thr Pro Lys Ala Ala Glu Thr Thr Glu Val Glu Pro Lys Thr Asp Ile
        195                200              205

Ser Glu Asp Ser Thr Ser Ala Asn Arg Pro Val Pro Asn Glu Ser Ala
        210                215              220

Ser Glu Glu Val Ser Ser Ala Ala Pro Ala Gln Ala Pro Ala Glu Lys
225                230              235              240

Glu Glu Thr Ser Ala Pro Ala Ala Gln Lys Ala Val Ala Asp Thr Thr
            245              250              255

Ser Val Ala Thr Ser Asn Gly Leu Ser Tyr Ala Pro Asn His Ala Tyr
        260                265              270

Asn Pro Met Asn Ala Gly Leu Gln Pro Gln Thr Ala Ala Phe Lys Glu
        275                280              285

Glu Val Ala Ser Ala Phe Gly Ile Thr Ser Phe Ser Gly Tyr Arg Pro
        290                295              300

Gly Asp Pro Gly Asp His Gly Lys Gly Leu Ala Ile Asp Phe Met Val
305                310              315              320

Pro Glu Asn Ser Ala Leu Gly Asp Gln Val Ala Gln Tyr Ala Ile Asp
            325              330              335

His Met Ala Glu Arg Gly Ile Ser Tyr Val Ile Trp Lys Gln Arg Phe
        340                345              350

Tyr Ala Pro Phe Ala Ser Ile Tyr Gly Pro Ala Tyr Thr Trp Asn Pro
        355                360              365

Met Pro Asp Arg Gly Ser Ile Thr Glu Asn His Tyr Asp His Val His
370                375                  380

Val Ser Phe Asn Ala
385

```
<210> SEQ ID NO 3
<211> LENGTH: 1182
<212> TYPE: DNA
<213> ORGANISM: Streptococcus pyogenes

<400> SEQUENCE: 3
```

| atgattatta ctaaaaagag cttatttgtg acaagtgtcg ctttgtcgtt agcacctttg | 60 |
|---|---|
| gcgacagcgc aggcacaaga gtggacacca cgatcggtta cagaaatcaa gtctgaactc | 120 |
| gtcctagttg ataatgtttt tactatata gtaaaatacg gtgacacttt aagcacaatt | 180 |
| gctgaagcaa tggggattga tgtgcatgtc ttaggagata ttaatcatat gctaatatt | 240 |
| gacttaattt ttccagacac gatcctaaca gcaaactaca accaacacgg tcaggcaacg | 300 |
| actttgacgg ttcaagcacc tgcttctagt ccatctagcg ttagtcatgt acctagcagt | 360 |
| gagccattac cccaagcatc tgccacctct caaccgactg ttcctatggc accatctgcg | 420 |
| acaccatctg atgtcccaac gacaccattc gcatctgcaa agccagatag ttctgtgaca | 480 |

```
gcgtcatctg agctcacatc gtcaacgaat gatgtttcga ctgagttgtc tagcgaatca      540
caaaagcagc cagaagtacc acaagaagca gttccaactc ctaaagcagc tgaaccgact      600
gaagtcgaac ctaagacaga catctcagaa gacccaactt cagctaatag gcctgtacct      660
aacgagagtg cttcagaaga agcttcttct gcggcccccag cacaagctcc agcagaaaaa      720
gaagaaacct ctcagatgtt aactgcgcca gcagcacaaa aagctgtagc tgacaccaca      780
agtgttgcaa cctcaaacgg cctttcttac gctccaaacc atgcctacaa tccaatgaat      840
gcagggcttc aaccacaaac agcagccttc aaagaagaag tggcttctgc ctttggtatt      900
acgtcattta gtggttaccg tccaggagat ccaggagatc atggtaaagg attagccatt      960
gactttatgg taccggttag ctctacgctt ggtgatcaag ttgctcaata tgccattgac     1020
catatggcag agcgtggtat ttcatacgtt atttggaaac agcgattcta tgcgccattt     1080
gcaagtattt acggaccagc ctacacatgg aaccccatgc cagatcgcgg cagtattaca     1140
gaaaaccatt atgatcatgt tcatgtctcc tttaatgctt aa                        1182
```

<210> SEQ ID NO 4  
<211> LENGTH: 393  
<212> TYPE: PRT  
<213> ORGANISM: Streptococcus pyogenes

<400> SEQUENCE: 4

```
Met Ile Ile Thr Lys Lys Ser Leu Phe Val Thr Ser Val Ala Leu Ser
  1               5                  10                  15

Leu Ala Pro Leu Ala Thr Ala Gln Ala Gln Glu Trp Thr Pro Arg Ser
                 20                  25                  30

Val Thr Glu Ile Lys Ser Glu Leu Val Leu Val Asp Asn Val Phe Thr
             35                  40                  45

Tyr Ile Val Lys Tyr Gly Asp Thr Leu Ser Thr Ile Ala Glu Ala Met
         50                  55                  60

Gly Ile Asp Val His Val Leu Gly Asp Ile Asn His Ile Ala Asn Ile
 65                  70                  75                  80

Asp Leu Ile Phe Pro Asp Thr Ile Leu Thr Ala Asn Tyr Asn Gln His
                 85                  90                  95

Gly Gln Ala Thr Thr Leu Thr Val Gln Ala Pro Ala Ser Ser Pro Ser
            100                 105                 110

Ser Val Ser His Val Pro Ser Ser Glu Pro Leu Pro Gln Ala Ser Ala
            115                 120                 125

Thr Ser Gln Pro Thr Val Pro Met Ala Pro Ser Ala Thr Pro Ser Asp
        130                 135                 140

Val Pro Thr Thr Pro Phe Ala Ser Ala Lys Pro Asp Ser Ser Val Thr
145                 150                 155                 160

Ala Ser Ser Glu Leu Thr Ser Thr Asn Asp Val Ser Thr Glu Leu
                165                 170                 175

Ser Ser Glu Ser Gln Lys Gln Pro Glu Val Pro Gln Glu Ala Val Pro
            180                 185                 190

Thr Pro Lys Ala Ala Glu Pro Thr Glu Val Pro Lys Thr Asp Ile
        195                 200                 205

Ser Glu Asp Pro Thr Ser Ala Asn Arg Pro Val Pro Asn Glu Ser Ala
    210                 215                 220

Ser Glu Glu Ala Ser Ser Ala Ala Pro Ala Gln Ala Pro Ala Glu Lys
225                 230                 235                 240

Glu Glu Thr Ser Gln Met Leu Thr Ala Pro Ala Ala Gln Lys Ala Val
```

245                 250                 255
Ala Asp Thr Thr Ser Val Ala Thr Ser Asn Gly Leu Ser Tyr Ala Pro
                260                 265                 270

Asn His Ala Tyr Asn Pro Met Asn Ala Gly Leu Gln Pro Gln Thr Ala
            275                 280                 285

Ala Phe Lys Glu Glu Val Ala Ser Ala Phe Gly Ile Thr Ser Phe Ser
        290                 295                 300

Gly Tyr Arg Pro Gly Asp Pro Gly Asp His Gly Lys Gly Leu Ala Ile
305                 310                 315                 320

Asp Phe Met Val Pro Val Ser Ser Thr Leu Gly Asp Gln Val Ala Gln
                325                 330                 335

Tyr Ala Ile Asp His Met Ala Glu Arg Gly Ile Ser Tyr Val Ile Trp
                340                 345                 350

Lys Gln Arg Phe Tyr Ala Pro Phe Ala Ser Ile Tyr Gly Pro Ala Tyr
            355                 360                 365

Thr Trp Asn Pro Met Pro Asp Arg Gly Ser Ile Thr Glu Asn His Tyr
        370                 375                 380

Asp His Val His Val Ser Phe Asn Ala
385                 390

<210> SEQ ID NO 5
<211> LENGTH: 1170
<212> TYPE: DNA
<213> ORGANISM: Streptococcus pyogenes

<400> SEQUENCE: 5
atgattatta ctaaaaagag cttatttgtg acaagtgtcg ctttgtcgtt agtacctttg        60
gcgacagcgc aggcacaaga gtggacacca cgatcggtta cagaaatcaa gtctgaactc       120
gtcctagttg ataatgtttt tacttatact gtaaaatacg gtgacacttt aagcacaatt       180
gctgaagcaa tggggattga tgtgcatgtc ttaggagata ttaatcatat tgctaatatt       240
gacctaattt ttccagacac gatcctaaca gcaaactaca atcaacacgg tcaggcaacg       300
aatttgacgg ttcaagcacc tgcttctagt ccagctagcg ttagtcatgt acctagcagt       360
gagccattac cccaagcatc tgccacctct caaccgactg ttcctatggc accacctgcg       420
acaccatctg atgtcccaac gacaccattc gcatctgcaa agccagatag ttctgtgaca       480
gcgtcatctg agctcacatc gtcaacgaat gatgtttcga ctgagttgtc tagcgaatca       540
caaaagcagc cagaagtacc acaagaagca gttccaactc ctaaagcagc tgaaacgact       600
gaagtcgaac taagacagac atctcagaa gccccaactt cagctaatag gcctgtacct       660
aacgagagtg cttcagaaga gtttcttct gcggccccag cacaagcccc agcagaaaaa       720
gaagaaacct ctgcgccagc agcacaaaaa gctgtagctg acaccacaag tgttgcaacc       780
tcaaatggcc tttcttacgc tccaaaccat gcctacaatc aatgaatgc agggcttcaa       840 ccacaaacag cagccttcaa agaagaagtg gcttctgcct ttggtattac gtcatttagt       900
ggttaccgtc caggtgatcc aggagatcat ggtaaaggtt tggccattga ttttatggtg       960
cctgaaaatt ctgctcttgg tgatcaagtt gctcaatatg ccattgacca tatggcagag      1020
cgtggtattt catacgttat ttggaaacag cgattctatg cgccatttgc aagtatttac      1080
ggaccagcct acacatggaa ccccatgcca gatcgcggca gtattacaga aaaccattat      1140
gatcatgttc atgtctcctt taatgcttaa                                       1170

<210> SEQ ID NO 6

-continued

```
<211> LENGTH: 389
<212> TYPE: PRT
<213> ORGANISM: Streptococcus pyogenes

<400> SEQUENCE: 6
```

| | | | | | | | | | | | | | | |
|---|---|---|---|---|---|---|---|---|---|---|---|---|---|---|
| Met | Ile | Ile | Thr | Lys | Lys | Ser | Leu | Phe | Val | Thr | Ser | Val | Ala | Leu | Ser |
| 1 | | | | 5 | | | | | 10 | | | | | 15 | |
| Leu | Val | Pro | Leu | Ala | Thr | Ala | Gln | Ala | Gln | Glu | Trp | Thr | Pro | Arg | Ser |
| | | | 20 | | | | | 25 | | | | | 30 | | |
| Val | Thr | Glu | Ile | Lys | Ser | Glu | Leu | Val | Leu | Val | Asp | Asn | Val | Phe | Thr |
| | | | | 35 | | | | | 40 | | | | 45 | | |
| Tyr | Thr | Val | Lys | Tyr | Gly | Asp | Thr | Leu | Ser | Thr | Ile | Ala | Glu | Ala | Met |
| | 50 | | | | | 55 | | | | | 60 | | | | |
| Gly | Ile | Asp | Val | His | Val | Leu | Gly | Asp | Ile | Asn | His | Ile | Ala | Asn | Ile |
| 65 | | | | | 70 | | | | | 75 | | | | | 80 |
| Asp | Leu | Ile | Phe | Pro | Asp | Thr | Ile | Leu | Thr | Ala | Asn | Tyr | Asn | Gln | His |
| | | | | 85 | | | | | 90 | | | | | 95 | |
| Gly | Gln | Ala | Thr | Asn | Leu | Thr | Val | Gln | Ala | Pro | Ala | Ser | Ser | Pro | Ala |
| | | | 100 | | | | | 105 | | | | | 110 | | |
| Ser | Val | Ser | His | Val | Pro | Ser | Ser | Glu | Pro | Leu | Pro | Gln | Ala | Ser | Ala |
| | | | | 115 | | | | | 120 | | | | 125 | | |
| Thr | Ser | Gln | Pro | Thr | Val | Pro | Met | Ala | Pro | Pro | Ala | Thr | Pro | Ser | Asp |
| | 130 | | | | | 135 | | | | | 140 | | | | |
| Val | Pro | Thr | Thr | Pro | Phe | Ala | Ser | Ala | Lys | Pro | Asp | Ser | Ser | Val | Thr |
| 145 | | | | | 150 | | | | | 155 | | | | | 160 |
| Ala | Ser | Ser | Glu | Leu | Thr | Ser | Ser | Thr | Asn | Asp | Val | Ser | Thr | Glu | Leu |
| | | | | 165 | | | | | 170 | | | | | 175 | |
| Ser | Ser | Glu | Ser | Gln | Lys | Gln | Pro | Glu | Val | Pro | Gln | Glu | Ala | Val | Pro |
| | | | 180 | | | | | 185 | | | | | 190 | | |
| Thr | Pro | Lys | Ala | Ala | Glu | Thr | Thr | Glu | Val | Glu | Pro | Lys | Thr | Asp | Ile |
| | | | | 195 | | | | | 200 | | | | 205 | | |
| Ser | Glu | Ala | Pro | Thr | Ser | Ala | Asn | Arg | Pro | Val | Pro | Asn | Glu | Ser | Ala |
| | 210 | | | | | 215 | | | | | 220 | | | | |
| Ser | Glu | Glu | Val | Ser | Ser | Ala | Ala | Pro | Ala | Gln | Ala | Pro | Ala | Glu | Lys |
| 225 | | | | | 230 | | | | | 235 | | | | | 240 |
| Glu | Glu | Thr | Ser | Ala | Pro | Ala | Ala | Gln | Lys | Ala | Val | Ala | Asp | Thr | Thr |
| | | | | 245 | | | | | 250 | | | | | 255 | |
| Ser | Val | Ala | Thr | Ser | Asn | Gly | Leu | Ser | Tyr | Ala | Pro | Asn | His | Ala | Tyr |
| | | | 260 | | | | | 265 | | | | | 270 | | |
| Asn | Pro | Met | Asn | Ala | Gly | Leu | Gln | Pro | Gln | Thr | Ala | Ala | Phe | Lys | Glu |
| | | | | 275 | | | | | 280 | | | | 285 | | |
| Glu | Val | Ala | Ser | Ala | Phe | Gly | Ile | Thr | Ser | Phe | Ser | Gly | Tyr | Arg | Pro |
| | 290 | | | | | 295 | | | | | 300 | | | | |
| Gly | Asp | Pro | Gly | Asp | His | Gly | Lys | Gly | Leu | Ala | Ile | Asp | Phe | Met | Val |
| 305 | | | | | 310 | | | | | 315 | | | | | 320 |
| Pro | Glu | Asn | Ser | Ala | Leu | Gly | Asp | Gln | Val | Ala | Gln | Tyr | Ala | Ile | Asp |
| | | | | 325 | | | | | 330 | | | | | 335 | |
| His | Met | Ala | Glu | Arg | Gly | Ile | Ser | Tyr | Val | Ile | Trp | Lys | Gln | Arg | Phe |
| | | | 340 | | | | | 345 | | | | | 350 | | |
| Tyr | Ala | Pro | Phe | Ala | Ser | Ile | Tyr | Gly | Pro | Ala | Tyr | Thr | Trp | Asn | Pro |
| | | | | 355 | | | | | 360 | | | | 365 | | |
| Met | Pro | Asp | Arg | Gly | Ser | Ile | Thr | Glu | Asn | His | Tyr | Asp | His | Val | His |
| | 370 | | | | | 375 | | | | | 380 | | | | |
| Val | Ser | Phe | Asn | Ala | | | | | | | | | | | |

-continued

<210> SEQ ID NO 7
<211> LENGTH: 1149
<212> TYPE: DNA
<213> ORGANISM: Streptococcus pyogenes

<400> SEQUENCE: 7

| | | | | | |
|---|---|---|---|---|---|
| atgattatta | ctaaaaagag | cttatttgtg | acaagtgtcg | ctttgtcgtt | agcacctttg | 60 |
| gcgacagcgc | aggcacaaga | gtggacacca | cgatcggtta | cagaaatcaa | gtctgaactc | 120 |
| gtcctagttg | ataatgtttt | tacttataca | gtaaaatacg | gtgacacttt | aagcacaatt | 180 |
| gctgaagcaa | tggggattga | tgtgcatgtc | ttaggagata | ttaatcatat | tgctaatatt | 240 |
| gacttaattt | ttccagacac | gatcctaaca | gcaaactaca | atcaacacgg | tcaggcaacg | 300 |
| actttgacgg | ttcaagcacc | tgcttctagt | ccagctagcg | ttagtcatgt | acctagcagt | 360 |
| gagccattac | cccaagcatc | tgccacctct | caaccgactg | ttcctatggc | accatctgcg | 420 |
| acaccattag | catctgcaaa | gccagatagt | tctgtgacag | cgtcatctga | gctcacatcg | 480 |
| tcaacgaatg | atgtttcgac | tgagtcgtct | agcgaatcac | aaaagcagcc | agaagtacca | 540 |
| caagaagcag | ttccaactcc | taaagcagct | gaaacgactg | aagtcgaacc | taagacagac | 600 |
| atctcagaag | acccaacttc | agctaatagg | cctgtaccta | acgagagtgc | ttcagaagaa | 660 |
| gtttcttctg | cggccccagc | acaagcccca | gcagaaaaag | aagaaacctc | tgcgccagca | 720 |
| gcacaaaaag | ctgtagctga | caccacaagt | gttgcaacct | caaacggcct | ttcttacgct | 780 |
| ccaaaccatg | cctacaatcc | aatgaatgca | gggcttcaac | cacaaacagc | agccttcaaa | 840 |
| gaagaagtgg | cttctgcctt | tggtattacg | tcatttagtg | gttaccgtcc | aggtgaccca | 900 |
| ggagatcatg | gtaaaggttt | ggccattgat | tttatggtgc | ctgaaaattc | tgctcttggt | 960 |
| gatcaagttg | ctcaatatgc | cattgaccat | atggcagagc | gtggtatttc | atacgttatt | 1020 |
| tggaaacagc | gattctatgc | gccatttgca | agtatttacg | gaccagctta | cacatggaac | 1080 |
| cccatgccag | atcgcggcag | tattacagaa | aaccattatg | atcatgttca | tgtctccttt | 1140 |
| aatgcttaa | | | | | | 1149 |

<210> SEQ ID NO 8
<211> LENGTH: 382
<212> TYPE: PRT
<213> ORGANISM: Streptococcus pyogenes

<400> SEQUENCE: 8

```
Met Ile Ile Thr Lys Lys Ser Leu Phe Val Thr Ser Val Ala Leu Ser
  1               5                  10                  15

Leu Ala Pro Leu Ala Thr Ala Gln Ala Gln Glu Trp Thr Pro Arg Ser
             20                  25                  30

Val Thr Glu Ile Lys Ser Glu Leu Val Leu Val Asp Asn Val Phe Thr
         35                  40                  45

Tyr Thr Val Lys Tyr Gly Asp Thr Leu Ser Thr Ile Ala Glu Ala Met
     50                  55                  60

Gly Ile Asp Val His Val Leu Gly Asp Ile Asn His Ile Ala Asn Ile
 65                  70                  75                  80

Asp Leu Ile Phe Pro Asp Thr Ile Leu Thr Ala Asn Tyr Asn Gln His
                 85                  90                  95

Gly Gln Ala Thr Thr Leu Thr Val Gln Ala Pro Ala Ser Ser Pro Ala
            100                 105                 110
```

```
Ser Val Ser His Val Pro Ser Ser Glu Pro Leu Pro Gln Ala Ser Ala
        115                 120                 125

Thr Ser Gln Pro Thr Val Pro Met Ala Pro Ser Ala Thr Pro Leu Ala
    130                 135                 140

Ser Ala Lys Pro Asp Ser Ser Val Thr Ala Ser Ser Glu Leu Thr Ser
145                 150                 155                 160

Ser Thr Asn Asp Val Ser Thr Glu Ser Ser Glu Ser Gln Lys Gln
                165                 170                 175

Pro Glu Val Pro Gln Glu Ala Val Pro Thr Pro Lys Ala Ala Glu Thr
            180                 185                 190

Thr Glu Val Glu Pro Lys Thr Asp Ile Ser Glu Asp Pro Thr Ser Ala
        195                 200                 205

Asn Arg Pro Val Pro Asn Glu Ser Ala Ser Glu Val Ser Ser Ala
    210                 215                 220

Ala Pro Ala Gln Ala Pro Ala Glu Lys Glu Glu Thr Ser Ala Pro Ala
225                 230                 235                 240

Ala Gln Lys Ala Val Ala Asp Thr Thr Ser Val Ala Thr Ser Asn Gly
                245                 250                 255

Leu Ser Tyr Ala Pro Asn His Ala Tyr Asn Pro Met Asn Ala Gly Leu
            260                 265                 270

Gln Pro Gln Thr Ala Ala Phe Lys Glu Glu Val Ala Ser Ala Phe Gly
        275                 280                 285

Ile Thr Ser Phe Ser Gly Tyr Arg Pro Gly Asp Pro Gly Asp His Gly
    290                 295                 300

Lys Gly Leu Ala Ile Asp Phe Met Val Pro Glu Asn Ser Ala Leu Gly
305                 310                 315                 320

Asp Gln Val Ala Gln Tyr Ala Ile Asp His Met Ala Glu Arg Gly Ile
                325                 330                 335

Ser Tyr Val Ile Trp Lys Gln Arg Phe Tyr Ala Pro Phe Ala Ser Ile
            340                 345                 350

Tyr Gly Pro Ala Tyr Thr Trp Asn Pro Met Pro Asp Arg Gly Ser Ile
        355                 360                 365

Thr Glu Asn His Tyr Asp His Val His Val Ser Phe Asn Ala
    370                 375                 380

<210> SEQ ID NO 9
<211> LENGTH: 1095
<212> TYPE: DNA
<213> ORGANISM: Streptococcus pyogenes

<400> SEQUENCE: 9
caagagtgga caccacgatc ggttacagaa atcaagtctg aactcgtcct agttgataat      60
gtttttactt atactgtaaa atacggtgac actttaagca caattgctga agcaatggga    120
attgatgtgc atgtcttagg agatattaat catattgcta atattgactt aatttttcca    180
gacacgatcc taacagccaa ctacaaccaa cacggtcagg caacgacttt gacggttcaa    240
gcgcctgctt ctagtccagc tagcgttagt catgtaccta gcagtgagcc attaccccaa    300
gcatctgcca cctctcaatc gactgttcct atggcaccat ctgcgacacc atctgatgtc    360
ccaacgacac cattcgcatc tgcaaagcca gatagttctg tgacagcgtc atctgagctc    420
acatcgtcaa cgaatgatgt ttcgactgag ttgtctagcg aatcacaaaa gcagccagaa    480
gtaccacaag aagcagttcc aactcctaaa gcagctgaaa cgactgaagt cgaacctaag    540
acagacatct cagaggattc aacttcagct aataggcctg tacctaacga gagtgcttca    600
```

```
gaagaagttt cttctgcggc cccagcacaa gccccagcag aaaaagaaga aacctctgcg    660
ccagcagcac aaaaagctgt agctgacacc acaagtgttg aacctcaaa tggcctttct    720 tacgctccaa accatgccta caatccaatg aatgcagggc ttcaaccaca aacagcagcc    780
ttcaaagaag aagtggcttc tgcctttggt attacgtcat ttagtggtta ccgtccaggt    840
gatccaggag atcatggtaa aggtttggcc attgatttta tggtgcctga aaattctgct    900
cttggtgatc aagttgctca atatgccatt gaccatatgg cagagcgtgg tatttcatac    960
gttatttgga aacagcgatt ctatgcgcca tttgcaagta tttacggacc agcctacaca   1020
tggaacccca tgccagatcg cggcagtatt acagaaaacc attatgatca tgttcatgtc   1080
tcctttaatg cttaa                                                     1095
```

<210> SEQ ID NO 10
<211> LENGTH: 364
<212> TYPE: PRT
<213> ORGANISM: Streptococcus pyogenes
<400> SEQUENCE: 10

```
Gln Glu Trp Thr Pro Arg Ser Val Thr Glu Ile Lys Ser Glu Leu Val
  1               5                  10                  15

Leu Val Asp Asn Val Phe Thr Tyr Thr Val Lys Tyr Gly Asp Thr Leu
             20                  25                  30

Ser Thr Ile Ala Glu Ala Met Gly Ile Asp Val His Val Leu Gly Asp
         35                  40                  45

Ile Asn His Ile Ala Asn Ile Asp Leu Ile Phe Pro Asp Thr Ile Leu
     50                  55                  60

Thr Ala Asn Tyr Asn Gln His Gly Gln Ala Thr Thr Leu Thr Val Gln
 65                  70                  75                  80

Ala Pro Ala Ser Ser Pro Ala Ser Val Ser His Val Pro Ser Ser Glu
                 85                  90                  95

Pro Leu Pro Gln Ala Ser Ala Thr Ser Gln Ser Thr Val Pro Met Ala
            100                 105                 110

Pro Ser Ala Thr Pro Ser Asp Val Pro Thr Thr Pro Phe Ala Ser Ala
        115                 120                 125

Lys Pro Asp Ser Ser Val Thr Ala Ser Ser Glu Leu Thr Ser Ser Thr
    130                 135                 140

Asn Asp Val Ser Thr Glu Leu Ser Ser Glu Ser Gln Lys Gln Pro Glu
145                 150                 155                 160

Val Pro Gln Glu Ala Val Pro Thr Pro Lys Ala Ala Glu Thr Thr Glu
                165                 170                 175

Val Glu Pro Lys Thr Asp Ile Ser Glu Asp Ser Thr Ser Ala Asn Arg
            180                 185                 190

Pro Val Pro Asn Glu Ser Ala Ser Glu Glu Val Ser Ser Ala Ala Pro
        195                 200                 205

Ala Gln Ala Pro Ala Glu Lys Glu Glu Thr Ser Ala Pro Ala Ala Gln
    210                 215                 220

Lys Ala Val Ala Asp Thr Thr Ser Val Ala Thr Ser Asn Gly Leu Ser
225                 230                 235                 240

Tyr Ala Pro Asn His Ala Tyr Asn Pro Met Asn Ala Gly Leu Gln Pro
                245                 250                 255

Gln Thr Ala Ala Phe Lys Glu Glu Val Ala Ser Ala Phe Gly Ile Thr
            260                 265                 270

Ser Phe Ser Gly Tyr Arg Pro Gly Asp Pro Gly Asp His Gly Lys Gly
        275                 280                 285
```

```
Leu Ala Ile Asp Phe Met Val Pro Glu Asn Ser Ala Leu Gly Asp Gln
    290                 295                 300

Val Ala Gln Tyr Ala Ile Asp His Met Ala Glu Arg Gly Ile Ser Tyr
305                 310                 315                 320

Val Ile Trp Lys Gln Arg Phe Tyr Ala Pro Phe Ala Ser Ile Tyr Gly
                325                 330                 335

Pro Ala Tyr Thr Trp Asn Pro Met Pro Asp Arg Gly Ser Ile Thr Glu
            340                 345                 350

Asn His Tyr Asp His Val His Val Ser Phe Asn Ala
        355                 360
```

```
<210> SEQ ID NO 11
<211> LENGTH: 1106
<212> TYPE: DNA
<213> ORGANISM: Streptococcus pyogenes

<400> SEQUENCE: 11
caagagtgga caccacgatc ggttacagaa atcaagtctg aactcgtcct agttgataat       60
gtttttactt atatagtaaa ataccggtga actttaagca caattgctga agcaatgggg      120
attgatgtgc atgtcttagg agatattaat catattgcta atattgactt aattttttcca    180
gacacgatcc taacagcaaa ctacaaccaa acggtcagg caacgacttt gacggttcaa       240
gcacctgctt ctagtccatc tagcgttagt catgtaccta gcagtgagcc attaccccaa      300
gcatctgcca cctctcaacc gactgttcct atggcaccat ctgcgacacc atctgatgtc      360
ccaacgacac cattcgcatc tgcaaagcca gatagttctg tgacagcgtc atctgagctc      420
acatcgtcaa cgaatgatgt ttcgactgag ttgtctagcg aatcacaaaa gcagccagaa      480
gtaccacaag aagcagttcc aactcctaaa gcagctgaac cgactgaagt cgaacctaag      540
acagacatct cagaagaccc aacttcagct aataggcctg acctaacgag agtgcttcag      600
aagaagcttc ttctgcggcc ccagcacaag ctccagcaga aaaagaagaa acctctcaga      660
tgttaactgc gccagcagca caaaaagctg tagctgacac cacaagtgtt gcaacctcaa      720
acggcctttc ttacgctcca aaccatgcct acaatccaat gaatgcaggg cttcaaccac      780
aaacagcagc cttcaaagaa gaagtggctt ctgcctttgg tattacgtca tttagtggtt      840
accgtccagg agatccagga gatcatggta aaggattagc cattgacttt atggtaccgg      900
ttagctctac gcttggtgat caagttgctc aatatgccat tgaccatatg gcagagcgtg      960
gtatttcata cgttatttgg aaacagcgat tctatgcgcc atttgcaagt atttacggac     1020
cagcctacac atggaacccc atgccagatc gcggcagtat tacagaaaac cattatgatc     1080
atgttcatgt ctccttttaat gcttaa                                          1106
```

```
<210> SEQ ID NO 12
<211> LENGTH: 368
<212> TYPE: PRT
<213> ORGANISM: Streptococcus pyogenes

<400> SEQUENCE: 12

Gln Glu Trp Thr Pro Arg Ser Val Thr Glu Ile Lys Ser Glu Leu Val
  1               5                  10                  15

Leu Val Asp Asn Val Phe Thr Tyr Ile Val Lys Tyr Gly Asp Thr Leu
                20                  25                  30

Ser Thr Ile Ala Glu Ala Met Gly Ile Asp Val His Val Leu Gly Asp
         35                  40                  45
```

-continued

```
Ile Asn His Ile Ala Asn Ile Asp Leu Ile Phe Pro Asp Thr Ile Leu
 50                  55                  60
Thr Ala Asn Tyr Asn Gln His Gly Gln Ala Thr Leu Thr Val Gln
 65                  70                  75                  80
Ala Pro Ala Ser Ser Pro Ser Ser Val Ser His Val Pro Ser Ser Glu
                 85                  90                  95
Pro Leu Pro Gln Ala Ser Ala Thr Ser Gln Pro Thr Val Pro Met Ala
                100                 105                 110
Pro Ser Ala Thr Pro Ser Asp Val Pro Thr Thr Pro Phe Ala Ser Ala
                115                 120                 125
Lys Pro Asp Ser Ser Val Thr Ala Ser Ser Glu Leu Thr Ser Ser Thr
                130                 135                 140
Asn Asp Val Ser Thr Glu Leu Ser Ser Glu Ser Gln Lys Gln Pro Glu
145                 150                 155                 160
Val Pro Gln Glu Ala Val Pro Thr Pro Lys Ala Ala Glu Pro Thr Glu
                165                 170                 175
Val Glu Pro Lys Thr Asp Ile Ser Glu Asp Pro Thr Ser Ala Asn Arg
                180                 185                 190
Pro Val Pro Asn Glu Ser Ala Ser Glu Glu Ala Ser Ser Ala Ala Pro
                195                 200                 205
Ala Gln Ala Pro Ala Glu Lys Glu Thr Ser Gln Met Leu Thr Ala
                210                 215                 220
Pro Ala Ala Gln Lys Ala Val Ala Asp Thr Thr Ser Val Ala Thr Ser
225                 230                 235                 240
Asn Gly Leu Ser Tyr Ala Pro Asn His Ala Tyr Asn Pro Met Asn Ala
                245                 250                 255
Gly Leu Gln Pro Gln Thr Ala Ala Phe Lys Glu Glu Val Ala Ser Ala
                260                 265                 270
Phe Gly Ile Thr Ser Phe Ser Gly Tyr Arg Pro Gly Asp Pro Gly Asp
                275                 280                 285
His Gly Lys Gly Leu Ala Ile Asp Phe Met Val Pro Val Ser Ser Thr
                290                 295                 300
Leu Gly Asp Gln Val Ala Gln Tyr Ala Ile Asp His Met Ala Glu Arg
305                 310                 315                 320
Gly Ile Ser Tyr Val Ile Trp Lys Gln Arg Phe Tyr Ala Pro Phe Ala
                325                 330                 335
Ser Ile Tyr Gly Pro Ala Tyr Thr Trp Asn Pro Met Pro Asp Arg Gly
                340                 345                 350
Ser Ile Thr Glu Asn His Tyr Asp His Val His Val Ser Phe Asn Ala
                355                 360                 365
```

<210> SEQ ID NO 13
<211> LENGTH: 1095
<212> TYPE: DNA
<213> ORGANISM: Streptococcus pyogenes

<400> SEQUENCE: 13

| | | |
|---|---|---|
| caagagtgga caccacgatc ggttacagaa atcaagtctg aactcgtcct agttgataat | 60 |
| gtttttactt atactgtaaa atacggtgac actttaagca caattgctga agcaatgggg | 120 |
| attgatgtgc atgtcttagg agatattaat catattgcta atattgacct aattttccca | 180 |
| gacacgatcc taacagcaaa ctacaatcaa cacggtcagg caacgaattt gacggttcaa | 240 |
| gcacctgctt ctagtccagc tagcgttagt catgtaccta gcagtgagcc attaccccaa | 300 |
| gcatctgcca cctctcaacc gactgttcct atggcaccac ctgcgacacc atctgatgtc | 360 |

```
ccaacgacac cattcgcatc tgcaaagcca gatagttctg tgacagcgtc atctgagctc      420
acatcgtcaa cgaatgatgt ttcgactgag ttgtctagcg aatcacaaaa gcagccagaa      480
gtaccacaag aagcagttcc aactcctaaa gcagctgaaa cgactgaagt cgaacctaag      540
acagacatct cagaagcccc aacttcagct aataggcctg tacctaacga gagtgcttca      600
gaagaagttt cttctgcggc cccagcacaa gccccagcag aaaaagaaga aacctctgcg      660
ccagcagcac aaaaagctgt agctgacacc acaagtgttg caacctcaaa tggcctttct      720
tacgctccaa accatgccta caatccaatg aatgcagggc ttcaaccaca aacagcagcc      780
ttcaaagaag aagtggcttc tgcctttggt attacgtcat ttagtggtta ccgtccaggt      840
gatccaggag atcatggtaa aggtttggcc attgatttta tggtgcctga aaattctgct      900
cttggtgatc aagttgctca atatgccatt gaccatatgg cagagcgtgg tatttcatac      960
gttatttgga acagcgatt ctatgcgcca tttgcaagta tttacggacc agcctacaca     1020
tggaacccca tgccagatcg cggcagtatt acagaaaacc attatgatca tgttcatgtc     1080
tcctttaatg cttaa                                                      1095
```

<210> SEQ ID NO 14
<211> LENGTH: 364
<212> TYPE: PRT
<213> ORGANISM: Streptococcus pyogenes

<400> SEQUENCE: 14

```
Gln Glu Trp Thr Pro Arg Ser Val Thr Glu Ile Lys Ser Glu Leu Val
  1               5                  10                  15

Leu Val Asp Asn Val Phe Thr Tyr Thr Val Lys Tyr Gly Asp Thr Leu
             20                  25                  30

Ser Thr Ile Ala Glu Ala Met Gly Ile Asp Val His Val Leu Gly Asp
         35                  40                  45

Ile Asn His Ile Ala Asn Ile Asp Leu Ile Phe Pro Asp Thr Ile Leu
     50                  55                  60

Thr Ala Asn Tyr Asn Gln His Gly Gln Ala Thr Asn Leu Thr Val Gln
 65                  70                  75                  80

Ala Pro Ala Ser Ser Pro Ala Ser Val Ser His Val Pro Ser Ser Glu
                 85                  90                  95

Pro Leu Pro Gln Ala Ser Ala Thr Ser Gln Pro Thr Val Pro Met Ala
            100                 105                 110

Pro Pro Ala Thr Pro Ser Asp Val Pro Thr Thr Pro Phe Ala Ser Ala
        115                 120                 125

Lys Pro Asp Ser Ser Val Thr Ala Ser Ser Glu Leu Thr Ser Ser Thr
    130                 135                 140

Asn Asp Val Ser Thr Glu Leu Ser Ser Glu Ser Gln Lys Gln Pro Glu
145                 150                 155                 160

Val Pro Gln Glu Ala Val Pro Thr Pro Lys Ala Ala Glu Thr Thr Glu
                165                 170                 175

Val Glu Pro Lys Thr Asp Ile Ser Glu Ala Pro Thr Ser Ala Asn Arg
            180                 185                 190

Pro Val Pro Asn Glu Ser Ala Ser Glu Val Ser Ala Ala Pro
        195                 200                 205

Ala Gln Ala Pro Ala Glu Lys Glu Glu Thr Ser Ala Pro Ala Ala Gln
    210                 215                 220

Lys Ala Val Ala Asp Thr Thr Ser Val Ala Thr Ser Asn Gly Leu Ser
225                 230                 235                 240
```

Tyr Ala Pro Asn His Ala Tyr Asn Pro Met Asn Ala Gly Leu Gln Pro
                245                 250                 255

Gln Thr Ala Ala Phe Lys Glu Glu Val Ala Ser Ala Phe Gly Ile Thr
        260                 265                 270

Ser Phe Ser Gly Tyr Arg Pro Gly Asp Pro Gly Asp His Gly Lys Gly
    275                 280                 285

Leu Ala Ile Asp Phe Met Val Pro Glu Asn Ser Ala Leu Gly Asp Gln
290                 295                 300

Val Ala Gln Tyr Ala Ile Asp His Met Ala Glu Arg Gly Ile Ser Tyr
305                 310                 315                 320

Val Ile Trp Lys Gln Arg Phe Tyr Ala Pro Phe Ala Ser Ile Tyr Gly
                325                 330                 335

Pro Ala Tyr Thr Trp Asn Pro Met Pro Asp Arg Gly Ser Ile Thr Glu
            340                 345                 350

Asn His Tyr Asp His Val His Val Ser Phe Asn Ala
        355                 360

<210> SEQ ID NO 15
<211> LENGTH: 1074
<212> TYPE: DNA
<213> ORGANISM: Streptococcus pyogenes

<400> SEQUENCE: 15
caagagtgga caccacgatc ggttacagaa atcaagtctg aactcgtcct agttgataat      60
gtttttactt atacagtaaa atacggtgac actttaagca caattgctga agcaatgggg     120
attgatgtgc atgtcttagg agatattaat catattgcta atattgactt aatttttcca     180
gacacgatcc taacagcaaa ctacaatcaa cacggtcagg caacgacttt gacggttcaa     240
gcacctgctt ctagtccagc tagcgttagt catgtaccta gcagtgagcc attaccccaa     300
gcatctgcca cctctcaacc gactgttcct atggcaccat ctgcgacacc attagcatct     360
gcaaagccag atagttctgt gacagcgtca tctgagctca catcgtcaac gaatgatgtt     420
tcgactgagt cgtctagcga atcacaaaag cagccagaag taccacaaga agcagttcca     480
actcctaaag cagctgaaac gactgaagtc gaacctaaga cagacatctc agaagaccca     540
acttcagcta ataggcctgt acctaacgag agtgcttcag aagaagtttc ttctgcggcc     600
ccagcacaag ccccagcaga aaagaagaa acctctgcgc agcagcaca aaaagctgta      660
gctgacacca aagtgttgc aacctcaaac ggcctttctt acgctccaaa ccatgcctac     720
aatccaatga atgcagggct tcaaccacaa acagcagcct caaagaaga gtggcttct      780
gcctttggta ttcgtcatt tagtggttac cgtccaggtg acccaggaga tcatggtaaa     840
ggtttggcca ttgatttat ggtgcctgaa aattctgctc ttggtgatca agttgctcaa     900
tatgccattg accatatggc agagcgtggt atttcatacg ttatttggaa acagcgattc     960
tatgcgccat ttgcaagtat ttacggacca gcttacacat ggaaccccat gccagatcgc    1020
ggcagtatta cagaaaacca ttatgatcat gttcatgtct cctttaatgc ttaa          1074

<210> SEQ ID NO 16
<211> LENGTH: 357
<212> TYPE: PRT
<213> ORGANISM: Streptococcus pyogenes

<400> SEQUENCE: 16

Gln Glu Trp Thr Pro Arg Ser Val Thr Glu Ile Lys Ser Glu Leu Val
1               5                   10                  15

Leu Val Asp Asn Val Phe Thr Tyr Thr Val Lys Tyr Gly Asp Thr Leu
            20                  25                  30

Ser Thr Ile Ala Glu Ala Met Gly Ile Asp Val His Val Leu Gly Asp
        35                  40                  45

Ile Asn His Ile Ala Asn Ile Asp Leu Ile Phe Pro Asp Thr Ile Leu
50                  55                  60

Thr Ala Asn Tyr Asn Gln His Gly Gln Ala Thr Thr Leu Thr Val Gln
65                  70                  75                  80

Ala Pro Ala Ser Pro Ala Ser Val Ser His Val Pro Ser Ser Glu
                85                  90                  95

Pro Leu Pro Gln Ala Ser Ala Thr Ser Gln Pro Thr Val Pro Met Ala
            100                 105                 110

Pro Ser Ala Thr Pro Leu Ala Ser Ala Lys Pro Asp Ser Ser Val Thr
            115                 120                 125

Ala Ser Ser Glu Leu Thr Ser Ser Thr Asn Asp Val Ser Thr Glu Ser
        130                 135                 140

Ser Ser Glu Ser Gln Lys Gln Pro Glu Val Pro Gln Glu Ala Val Pro
145                 150                 155                 160

Thr Pro Lys Ala Ala Glu Thr Thr Glu Val Glu Pro Lys Thr Asp Ile
                165                 170                 175

Ser Glu Asp Pro Thr Ser Ala Asn Arg Pro Val Pro Asn Glu Ser Ala
            180                 185                 190

Ser Glu Glu Val Ser Ser Ala Ala Pro Ala Gln Ala Pro Ala Glu Lys
        195                 200                 205

Glu Glu Thr Ser Ala Pro Ala Ala Gln Lys Ala Val Ala Asp Thr Thr
210                 215                 220

Ser Val Ala Thr Ser Asn Gly Leu Ser Tyr Ala Pro Asn His Ala Tyr
225                 230                 235                 240

Asn Pro Met Asn Ala Gly Leu Gln Pro Gln Thr Ala Ala Phe Lys Glu
                245                 250                 255

Glu Val Ala Ser Ala Phe Gly Ile Thr Ser Phe Ser Gly Tyr Arg Pro
            260                 265                 270

Gly Asp Pro Gly Asp His Gly Lys Gly Leu Ala Ile Asp Phe Met Val
        275                 280                 285

Pro Glu Asn Ser Ala Leu Gly Asp Gln Val Ala Gln Tyr Ala Ile Asp
290                 295                 300

His Met Ala Glu Arg Gly Ile Ser Tyr Val Ile Trp Lys Gln Arg Phe
305                 310                 315                 320

Tyr Ala Pro Phe Ala Ser Ile Tyr Gly Pro Ala Tyr Thr Trp Asn Pro
                325                 330                 335

Met Pro Asp Arg Gly Ser Ile Thr Glu Asn His Tyr Asp His Val His
            340                 345                 350

Val Ser Phe Asn Ala
        355

<210> SEQ ID NO 17
<211> LENGTH: 1113
<212> TYPE: DNA
<213> ORGANISM: Streptococcus pneumonia

<400> SEQUENCE: 17
atgaagaaaa gaatgttatt agcgtcaaca gtagccttgt catttgcccc agtattggca    60
actcaagcag aagaagttct ttggactgca cgtagtgttg agcaaatcca aaacgatttg   120

-continued

```
actaaaacgg acaacaaaac aagttatacc gtacagtatg gtgatacttt gagcaccatt    180
gcagaagcct tgggtgtaga tgtcacagtg cttgcgaatc tgaacaaaat cactaatatg    240
gacttgattt tcccagaaac tgttttgaca acgactgtca atgaagcaga agaagtaaca    300
gaagttgaaa tccaaacacc tcaagcagac tctagtgaag aagtgacaac tgcgacagca    360
gatttgacca ctaatcaagt gaccgttgat gatcaaactg ttcaggttgc agacctttct    420
caaccaattg cagaagttac aaagacagtg attgcttctg aagaagtggc accatctacg    480
ggcacttctg tcccagagga gcaaacgacc gaaacaactc gcccagttga agaagcaact    540
cctcaggaaa cgactccagc tgagaagcag aaacacaag caagccctca agctgcatca    600
gcagtggaag taactacaac aagttcagaa gcaaagaag tagcatcatc aaatggagct    660
acagcagcag tttctactta tcaaccagaa gagacgaaaa taatttcaac aacttacgag    720
gctccagctg cgcccgatta tgctggactt gcagtagcaa atctgaaaaa tgcaggtctt    780
caaccacaaa cagctgcctt taagaagaa attgctaact tgtttggcat acatcctttt    840
agtggttatc gtccaggaga cagtggagat cacggaaaag gtttggctat cgactttatg    900
gtaccagaac gttcagaatt aggggataag attgcgaat atgctattca aaatatggcc    960
agccgtggca ttagttacat catctggaaa caacgtttct atgctccatt cgatagcaaa   1020
tatgggccag ctaacacttg gaacccaatg ccagaccgtg gtagtgtgac agaaaaatcac  1080 tatgatcacg ttcacgtttc aatgaatgga taa                                1113
```

<210> SEQ ID NO 18
<211> LENGTH: 370
<212> TYPE: PRT
<213> ORGANISM: Streptococcus pneumonia

<400> SEQUENCE: 18

```
Met Lys Lys Arg Met Leu Leu Ala Ser Thr Val Ala Leu Ser Phe Ala
  1               5                  10                  15

Pro Val Leu Ala Thr Gln Ala Glu Glu Val Leu Trp Thr Ala Arg Ser
                 20                  25                  30

Val Glu Gln Ile Gln Asn Asp Leu Thr Lys Thr Asp Asn Lys Thr Ser
             35                  40                  45

Tyr Thr Val Gln Tyr Gly Asp Thr Leu Ser Thr Ile Ala Glu Ala Leu
         50                  55                  60

Gly Val Asp Val Thr Val Leu Ala Asn Leu Asn Lys Ile Thr Asn Met
 65                  70                  75                  80

Asp Leu Ile Phe Pro Glu Thr Val Leu Thr Thr Val Asn Glu Ala
                 85                  90                  95

Glu Glu Val Thr Glu Val Glu Ile Gln Thr Pro Gln Ala Asp Ser Ser
            100                 105                 110

Glu Glu Val Thr Thr Ala Thr Ala Asp Leu Thr Thr Asn Gln Val Thr
            115                 120                 125

Val Asp Asp Gln Thr Val Gln Val Ala Asp Leu Ser Gln Pro Ile Ala
        130                 135                 140

Glu Val Thr Lys Thr Val Ile Ala Ser Glu Glu Val Ala Pro Ser Thr
145                 150                 155                 160

Gly Thr Ser Val Pro Glu Glu Gln Thr Thr Glu Thr Thr Arg Pro Val
                165                 170                 175

Glu Glu Ala Thr Pro Gln Glu Thr Thr Pro Ala Glu Lys Gln Glu Thr
            180                 185                 190

Gln Ala Ser Pro Gln Ala Ala Ser Ala Val Glu Val Thr Thr Thr Ser
```

-continued

```
            195                 200                 205
Ser Glu Ala Lys Glu Val Ala Ser Ser Asn Gly Ala Thr Ala Ala Val
    210                 215                 220

Ser Thr Tyr Gln Pro Glu Glu Thr Lys Ile Ile Ser Thr Thr Tyr Glu
225                 230                 235                 240

Ala Pro Ala Ala Pro Asp Tyr Ala Gly Leu Ala Val Ala Lys Ser Glu
                245                 250                 255

Asn Ala Gly Leu Gln Pro Gln Thr Ala Ala Phe Lys Glu Glu Ile Ala
            260                 265                 270

Asn Leu Phe Gly Ile Thr Ser Phe Ser Gly Tyr Arg Pro Gly Asp Ser
        275                 280                 285

Gly Asp His Gly Lys Gly Leu Ala Ile Asp Phe Met Val Pro Glu Arg
    290                 295                 300

Ser Glu Leu Gly Asp Lys Ile Ala Glu Tyr Ala Ile Gln Asn Met Ala
305                 310                 315                 320

Ser Arg Gly Ile Ser Tyr Ile Ile Trp Lys Gln Arg Phe Tyr Ala Pro
                325                 330                 335

Phe Asp Ser Lys Tyr Gly Pro Ala Asn Thr Trp Asn Pro Met Pro Asp
            340                 345                 350

Arg Gly Ser Val Thr Glu Asn His Tyr Asp His Val His Val Ser Met
        355                 360                 365

Asn Gly
    370

<210> SEQ ID NO 19
<211> LENGTH: 1183
<212> TYPE: DNA
<213> ORGANISM: Streptococcus pyogenes
<220> FEATURE:
<221> NAME/KEY: misc_difference
<222> LOCATION: 428)...(448)
<223> OTHER INFORMATION: May be ctgatgtcccaacgacaccat or absent
<220> FEATURE:
<221> NAME/KEY: misc_difference
<222> LOCATION: (733)...(744)
<223> OTHER INFORMATION: May be cagatgttaact or absent
<220> FEATURE:
<221> NAME/KEY: misc_difference
<222> LOCATION: (883)...(883)
<223> OTHER INFORMATION: g or absent
<220> FEATURE:
<221> NAME/KEY: misc_difference
<222> LOCATION: (943)...(943)
<223> OTHER INFORMATION: t or absent

<400> SEQUENCE: 19
atgattatta ctaaaaagag yttatttgtg acaagtgtcg ctttgtcgtt agyacctttg      60
gcgacagcrc aggcacaaga gtggacacca cgatcggtta casaaatcaa gtctgaactc     120
gtcctagttg ataatgtttt tacttatayw gtaaaatacg gtgacacttt aagcacaatt     180
gctgaagcaa tgggrattga tgtgcatgtc ttaggagata ttaatcatat tgctaatatt     240
gacytaattt ttccagacac gatcctaaca gcmaactaca aycaacacgg tcaggcaacg     300
amtttgacgg ttcaagcrcc tgcttctagt ccakctagcg ttagtcatgt acctagcagt     360
gagccattac cccaagcatc tgccacctct caaycgactr ttcctatggc accayctgcg     420
acaccatnnn nnnnnnnnn nnnnnnnntm gcatctgcaa agccagatag ttytgtgaca     480
gcgtcatctg agctcacatc rtcaacgaat gatgtttcga ctgagtygtc tagcgaatca     540
caaaagcagc cagaagtacc acaagaagca gwwccaactc ctaaagcagc tgaamssact     600
```

-continued

```
gaagtcgaac ctaagacaga catctcagar gmyycaactt cagctaatag gcctgtacct    660
aacgrragtg cttcagaaga agyttcttct gcggccccag cacaagcycc agcagaaaaa    720
gaagaaacct ctnnnnnnnn nnnngcgcca gcagcacaaa aagctgtagc tgacaccaca    780
agtgttgcaa cctcaaaygg cctttcttac gctccaaacc atgcctacaa tccaatgaat    840
gcagggcttc aaccacaaac agcagccttc aaagaagaag tgncttctgc ctttggtatt    900
acgtcattta gtggttaccg tccaggwgay ccaggagatc atnggtaaag gwttrgccat    960
tgaytttatg gtrcckgwwa rytctrckct tggtgatcaa gttgctcaat atgccattga   1020
ccatatggca gassgtggta tttcatacgt tatttggaaa cagcgattct atgcgccatt   1080
tgcaagtatt tacggaccag cytacacatg gaacccatg ccagatcgcg gcagtattac   1140
agwwwwccat tatgatcatg ttcatgtctc ctttaatgct taa                     1183
```

```
<210> SEQ ID NO 20
<211> LENGTH: 393
<212> TYPE: PRT
<213> ORGANISM: Streptococcus pyogenes
<220> FEATURE:
<221> NAME/KEY: VARIANT
<222> LOCATION: (18)...(18)
<223> OTHER INFORMATION: Xaa = Ala or Val
<220> FEATURE:
<221> NAME/KEY: VARIANT
<222> LOCATION: (50)...(50)
<223> OTHER INFORMATION: Xaa = Thr or Ile
<220> FEATURE:
<221> NAME/KEY: VARIANT
<222> LOCATION: (101)...(101)
<223> OTHER INFORMATION: Xaa = Thr or Asn
<220> FEATURE:
<221> NAME/KEY: VARIANT
<222> LOCATION: (112)...(112)
<223> OTHER INFORMATION: Xaa = Ala or Ser
<220> FEATURE:
<221> NAME/KEY: VARIANT
<222> LOCATION: (132)...(132)
<223> OTHER INFORMATION: Xaa = Pro or Ser
<220> FEATURE:
<221> NAME/KEY: VARIANT
<222> LOCATION: (134)...(134)
<223> OTHER INFORMATION: Xaa = Val or Ile
<220> FEATURE:
<221> NAME/KEY: VARIANT
<222> LOCATION: (139)...(139)
<223> OTHER INFORMATION: Xaa = Ser or Pro
<220> FEATURE:
<221> NAME/KEY: VARIANT
<222> LOCATION: (143)...(149)
<223> OTHER INFORMATION: May be Ser Asp Val Pro Thr Thr Pro or absent
<220> FEATURE:
<221> NAME/KEY: VARIANT
<222> LOCATION: (150)...(150)
<223> OTHER INFORMATION: Xaa = Phe or Leu
<220> FEATURE:
<221> NAME/KEY: VARIANT
<222> LOCATION: (158)...(158)
<223> OTHER INFORMATION: Xaa = Ser or Phe
<220> FEATURE:
<221> NAME/KEY: VARIANT
<222> LOCATION: (176)...(176)
<223> OTHER INFORMATION: Xaa = Leu or Ser
<220> FEATURE:
<221> NAME/KEY: VARIANT
<222> LOCATION: (191)...(191)
<223> OTHER INFORMATION: Xaa = Val or Glu
<220> FEATURE:
<221> NAME/KEY: VARIANT
<222> LOCATION: (199)...(199)
<223> OTHER INFORMATION: Xaa = Thr or Pro or Ser
<220> FEATURE:
<221> NAME/KEY: VARIANT
```

```
<222> LOCATION: (211)...(211)
<223> OTHER INFORMATION: Xaa = Asp or Ala
<220> FEATURE:
<221> NAME/KEY: VARIANT
<222> LOCATION: (212)...(212)
<223> OTHER INFORMATION: Xaa = Pro or Ser
<220> FEATURE:
<221> NAME/KEY: VARIANT
<222> LOCATION: (222)...(222)
<223> OTHER INFORMATION: Xaa = Glu or Gly
<220> FEATURE:
<221> NAME/KEY: VARIANT
<222> LOCATION: (228)...(228)
<223> OTHER INFORMATION: Xaa = Val or Ala
<220> FEATURE:
<221> NAME/KEY: VARIANT
<222> LOCATION: (242)...(245)
<223> OTHER INFORMATION: May be Glu Thr Ser Gln or absent
<220> FEATURE:
<221> NAME/KEY: VARIANT
<222> LOCATION: (246)...(246)
<223> OTHER INFORMATION: Xaa = Glu or Met
<220> FEATURE:
<221> NAME/KEY: VARIANT
<222> LOCATION: (247)...(247)
<223> OTHER INFORMATION: Xaa = Thr or Leu
<220> FEATURE:
<221> NAME/KEY: VARIANT
<222> LOCATION: (248)...(248)
<223> OTHER INFORMATION: Xaa = Ser or Thr
<220> FEATURE:
<221> NAME/KEY: VARIANT
<222> LOCATION: (295)...(295)
<223> OTHER INFORMATION: Xaa = Ala or Leu
<220> FEATURE:
<221> NAME/KEY: VARIANT
<222> LOCATION: (296)...(296)
<223> OTHER INFORMATION: Xaa = Ser or Leu
<220> FEATURE:
<221> NAME/KEY: VARIANT
<222> LOCATION: (297)...(297)
<223> OTHER INFORMATION: Xaa = Ala or Pro
<220> FEATURE:
<221> NAME/KEY: VARIANT
<222> LOCATION: (298)...(298)
<223> OTHER INFORMATION: Xaa = Phe or Leu
<220> FEATURE:
<221> NAME/KEY: VARIANT
<222> LOCATION: (299)...(299)
<223> OTHER INFORMATION: Xaa = Gly or Val
<220> FEATURE:
<221> NAME/KEY: VARIANT
<222> LOCATION: (300)...(300)
<223> OTHER INFORMATION: Xaa = Ile or Leu
<220> FEATURE:
<221> NAME/KEY: VARIANT
<222> LOCATION: (301)...(301)
<223> OTHER INFORMATION: Xaa = Thr or Arg
<220> FEATURE:
<221> NAME/KEY: VARIANT
<222> LOCATION: (302)...(302)
<223> OTHER INFORMATION: Xaa = Ser or His
<220> FEATURE:
<221> NAME/KEY: VARIANT
<222> LOCATION: (303)...(303)
<223> OTHER INFORMATION: Xaa = Phe or Leu
<220> FEATURE:
<221> NAME/KEY: VARIANT
<222> LOCATION: (304)...(304)
<223> OTHER INFORMATION: Xaa = Ser or Val
<220> FEATURE:
<221> NAME/KEY: VARIANT
<222> LOCATION: (305)...(305)
<223> OTHER INFORMATION: Xaa = Gly or Val
<220> FEATURE:
<221> NAME/KEY: VARIANT
<222> LOCATION: (306)...(306)
<223> OTHER INFORMATION: Xaa = Tyr or Thr
<220> FEATURE:
```

```
<221> NAME/KEY: VARIANT
<222> LOCATION: (307)...(307)
<223> OTHER INFORMATION: Xaa = Arg or Val
<220> FEATURE:
<221> NAME/KEY: VARIANT
<222> LOCATION: (308)...(308)
<223> OTHER INFORMATION: Xaa = Pro or Gln
<220> FEATURE:
<221> NAME/KEY: VARIANT
<222> LOCATION: (309)...(309)
<223> OTHER INFORMATION: Xaa = Gly or Glu
<220> FEATURE:
<221> NAME/KEY: VARIANT
<222> LOCATION: (310)...(310)
<223> OTHER INFORMATION: Xaa = Asp or Ile
<220> FEATURE:
<221> NAME/KEY: VARIANT
<222> LOCATION: (311)...(311)
<223> OTHER INFORMATION: Xaa = Pro or Gln
<220> FEATURE:
<221> NAME/KEY: VARIANT
<222> LOCATION: (312)...(312)
<223> OTHER INFORMATION: Xaa = Gly or Glu
<220> FEATURE:
<221> NAME/KEY: VARIANT
<222> LOCATION: (313)...(313)
<223> OTHER INFORMATION: Xaa = Asn or Ile
<220> FEATURE:
<221> NAME/KEY: VARIANT
<222> LOCATION: (314)...(314)
<223> OTHER INFORMATION: Xaa = His or Ile
<220> FEATURE:
<221> NAME/KEY: VARIANT
<222> LOCATION: (326)...(326)
<223> OTHER INFORMATION: Xaa = Glu or Val
<220> FEATURE:
<221> NAME/KEY: VARIANT
<222> LOCATION: (327)...(327)
<223> OTHER INFORMATION: Xaa = Asn or Ser
<220> FEATURE:
<221> NAME/KEY: VARIANT
<222> LOCATION: (329)...(329)
<223> OTHER INFORMATION: Xaa = Ala or Thr
<220> FEATURE:
<221> NAME/KEY: VARIANT
<222> LOCATION: (344)...(344)
<223> OTHER INFORMATION: Xaa = Glu or Asp
<220> FEATURE:
<221> NAME/KEY: VARIANT
<222> LOCATION: (345)...(345)
<223> OTHER INFORMATION: Xaa = Arg or Gly
<220> FEATURE:
<221> NAME/KEY: VARIANT
<222> LOCATION: (381)...(381)
<223> OTHER INFORMATION: Xaa = Glu or Val
<220> FEATURE:
<221> NAME/KEY: VARIANT
<222> LOCATION: (382)...(382)
<223> OTHER INFORMATION: Xaa = Asn or Phe

<400> SEQUENCE: 20

Met Ile Ile Thr Lys Lys Ser Leu Phe Val Thr Ser Val Ala Leu Ser
 1               5                  10                  15

Leu Xaa Pro Leu Ala Thr Ala Gln Ala Gln Glu Trp Thr Pro Arg Ser
                20                  25                  30

Val Thr Glx Ile Lys Ser Glu Leu Val Leu Val Asp Asn Val Phe Thr
            35                  40                  45

Tyr Xaa Val Lys Tyr Gly Asp Thr Leu Ser Thr Ile Ala Glu Ala Met
        50                  55                  60

Gly Ile Asp Val His Val Leu Gly Asp Ile Asn His Ile Ala Asn Ile
65                  70                  75                  80

Asp Leu Ile Phe Pro Asp Thr Ile Leu Thr Ala Asn Tyr Asn Gln His
                85                  90                  95
```

-continued

```
Gly Gln Ala Thr Xaa Leu Thr Val Gln Ala Pro Ala Ser Ser Pro Xaa
                100                 105                 110

Ser Val Ser His Val Pro Ser Ser Glu Pro Leu Pro Gln Ala Ser Ala
            115                 120                 125

Thr Ser Gln Xaa Thr Xaa Pro Met Ala Pro Xaa Ala Thr Pro Xaa Xaa
        130                 135                 140

Xaa Xaa Xaa Xaa Xaa Xaa Ala Ser Ala Lys Pro Asp Ser Xaa Val Thr
145                 150                 155                 160

Ala Ser Ser Glu Leu Thr Ser Ser Thr Asn Asp Val Ser Thr Glu Xaa
                165                 170                 175

Ser Ser Glu Ser Gln Lys Gln Pro Glu Val Pro Gln Glu Ala Xaa Pro
            180                 185                 190

Thr Pro Lys Ala Ala Glu Xaa Thr Glu Val Glu Pro Lys Thr Asp Ile
        195                 200                 205

Ser Glu Xaa Xaa Thr Ser Ala Asn Arg Pro Val Pro Asn Xaa Ser Ala
    210                 215                 220

Ser Glu Glu Xaa Ser Ser Ala Ala Pro Ala Gln Ala Pro Ala Glu Lys
225                 230                 235                 240

Glu Xaa Xaa Xaa Xaa Xaa Xaa Ala Pro Ala Ala Gln Lys Ala Val
                245                 250                 255

Ala Asp Thr Thr Ser Val Ala Thr Ser Asn Gly Leu Ser Tyr Ala Pro
                260                 265                 270

Asn His Ala Tyr Asn Pro Met Asn Ala Gly Leu Gln Pro Gln Thr Ala
            275                 280                 285

Ala Phe Lys Glu Glu Val Xaa Xaa Xaa Xaa Xaa Xaa Xaa Xaa Xaa
        290                 295                 300

Xaa Xaa Xaa Xaa Xaa Xaa Xaa Xaa Xaa Gly Lys Gly Leu Ala Ile
305                 310                 315                 320

Asp Phe Met Val Pro Xaa Xaa Ser Xaa Leu Gly Asp Gln Val Ala Gln
                325                 330                 335

Tyr Ala Ile Asp His Met Ala Xaa Xaa Gly Ile Ser Tyr Val Ile Trp
                340                 345                 350

Lys Gln Arg Phe Tyr Ala Pro Phe Ala Ser Ile Tyr Gly Pro Ala Tyr
            355                 360                 365

Thr Trp Asn Pro Met Pro Asp Arg Gly Ser Ile Thr Xaa Xaa His Tyr
        370                 375                 380

Asp His Val His Val Ser Phe Asn Ala
385                 390
```

<210> SEQ ID NO 21
<211> LENGTH: 32
<212> TYPE: DNA
<213> ORGANISM: Artificial Sequence
<220> FEATURE:
<223> OTHER INFORMATION: Synthetic DMAR16 Oligonucleotide

<400> SEQUENCE: 21
caggccatgg agtggacacc acgatcggtt ac                         32

<210> SEQ ID NO 22
<211> LENGTH: 37
<212> TYPE: DNA
<213> ORGANISM: Artificial Sequence
<220> FEATURE:
<223> OTHER INFORMATION: Synthetic DMAR17 Oligonucleotide

<400> SEQUENCE: 22

```
gccgctcgag agcattaaag gagacatgaa catgatc                                    37
```

<210> SEQ ID NO 23
<211> LENGTH: 25
<212> TYPE: PRT
<213> ORGANISM: Artificial Sequence
<220> FEATURE:
<223> OTHER INFORMATION: Predicted signal peptide from analysis of
      SEQ ID NO: 2

<400> SEQUENCE: 23

Met Ile Ile Thr Lys Lys Ser Leu Phe Val Thr Ser Val Ala Leu Ser
1               5                   10                  15

Leu Ala Pro Leu Ala Thr Ala Gln Ala
            20                  25

<210> SEQ ID NO 24
<211> LENGTH: 5
<212> TYPE: PRT
<213> ORGANISM: Artificial Sequence
<220> FEATURE:
<223> OTHER INFORMATION: Synthetic cell wall anchoring motif
<220> FEATURE:
<221> NAME/KEY: VARIANT
<222> LOCATION: (3)...(3)
<223> OTHER INFORMATION: Xaa = Any Amino Acid

<400> SEQUENCE: 24

Leu Pro Xaa Thr Gly
1               5

<210> SEQ ID NO 25
<211> LENGTH: 6
<212> TYPE: PRT
<213> ORGANISM: Artificial Sequence
<220> FEATURE:
<223> OTHER INFORMATION: Predicted IgA binding motif

<400> SEQUENCE: 25

Met Leu Lys Lys Ile Glu
1               5

<210> SEQ ID NO 26
<211> LENGTH: 28
<212> TYPE: DNA
<213> ORGANISM: Artificial Sequence
<220> FEATURE:
<223> OTHER INFORMATION: Synthetic DMAR69 oligonucleotide

<400> SEQUENCE: 26

```
ctgggaagat tatctagcac attaatac                                              28
```

<210> SEQ ID NO 27
<211> LENGTH: 25
<212> TYPE: DNA
<213> ORGANISM: Artificial Sequence
<220> FEATURE:
<223> OTHER INFORMATION: Synthetic DMAR72 oligonucleotide

<400> SEQUENCE: 27

```
cataacgtta aaactgtcta aaggg                                                 25
```

<210> SEQ ID NO 28
<211> LENGTH: 34
<212> TYPE: DNA
<213> ORGANISM: Artificial Sequence

```
<220> FEATURE:
<223> OTHER INFORMATION: Synthetic DMAR24 oligonucleotide

<400> SEQUENCE: 28
tacccggatc cccaagagtg gacaccacga tcgg                              34

<210> SEQ ID NO 29
<211> LENGTH: 36
<212> TYPE: DNA
<213> ORGANISM: Artificial Sequence
<220> FEATURE:
<223> OTHER INFORMATION: Synthetic DMAR25 oligonucleotide

<400> SEQUENCE: 29
gcgctcgtcg acgcgtatct cagcctctta tagggc                            36

<210> SEQ ID NO 30
<211> LENGTH: 1182
<212> TYPE: DNA
<213> ORGANISM: Streptococcus pyogenes

<400> SEQUENCE: 30
atgattatta ctaaaaagag tttatttgtg acaagtgtcg ctttgtcgtt agcacctttg    60
gcgacagcgc aggcacaaga gtggacacca cgatcggtta cacaaatcaa gtctgaactc   120
gtcctagttg ataatgtttt tacttataca gtaaaatacg gtgacacttt aagcacaatt   180
gctgaagcaa tggggattga tgtgcatgtc ttaggagata ttaatcatat tgctaatatt   240
gacttaattt ttccagacac gatcctaaca gcaaactaca accaacacgg tcaggcaacg   300
actttgacgg ttcaagcgcc tgcttctagt ccagctagcg ttagtcatgt acctagcagt   360
gagccattac cccaagcatc tgccacctct caatcgacta ttcctatggc accatctgcg   420
acaccatctg atgtcccaac gacaccatta gcatctgcaa agccagatag ttttgtgaca   480
gcgtcatctg agctcacatc atcaacgaat gatgtttcga ctgagttgtc tagcgaatca   540
caaaagcagc cagaagtacc acaagaagca gaaccaactc ctaaagcagc tgaaagcact   600
gaagtcgaac ctaagacaga catctcagaa gattcaactt cagctaatag gcctgtacct   660
aacggaagtg cttcagaaga agcttcttct gcggccccag cacaagctcc agcagaaaaa   720
gaagaaacct ctcagatgtt aactgcgcca gcagcacaaa agctgtagc tgacaccaca   780 agtgttgcaa cctcaaacgg ccttcttac gctccaaacc atgcctacaa tccaatgaat   840
gcagggcttc aaccacaaac agcagcttc aaagaagaag tgcttctgcc tttggtatta   900
cgtcatttag tggttaccgt ccaggagatc caggagatca ttggtaaagg attagccatt   960
gactttatgg taccggttag ctctacgctt ggtgatcaag ttgctcaata tgccattgac  1020
catatggcag acggtggtat ttcatacgtt atttggaaac agcgattcta tgcgccattt  1080
gcaagtattt acggaccagc ctacacatgg aaccccatgc agatcgcgg cagtattaca  1140 gttttccatt atgatcatgt tcatgtctcc tttaatgctt aa                     1182

<210> SEQ ID NO 31
<211> LENGTH: 393
<212> TYPE: PRT
<213> ORGANISM: Streptococcus pyogenes

<400> SEQUENCE: 31

Met Ile Ile Thr Lys Lys Ser Leu Phe Val Thr Ser Val Ala Leu Ser
 1               5                  10                  15

Leu Ala Pro Leu Ala Thr Ala Gln Ala Gln Glu Trp Thr Pro Arg Ser
```

```
                20                  25                  30
Val Thr Gln Ile Lys Ser Glu Leu Val Leu Val Asp Asn Val Phe Thr
            35                  40                  45

Tyr Thr Val Lys Tyr Gly Asp Thr Leu Ser Thr Ile Ala Glu Ala Met
 50                  55                  60

Gly Ile Asp Val His Val Leu Gly Asp Ile Asn His Ile Ala Asn Ile
 65                  70                  75                  80

Asp Leu Ile Phe Pro Asp Thr Ile Leu Thr Ala Asn Tyr Asn Gln His
                 85                  90                  95

Gly Gln Ala Thr Thr Leu Thr Val Gln Ala Pro Ala Ser Ser Pro Ala
            100                 105                 110

Ser Val Ser His Val Pro Ser Ser Glu Pro Leu Pro Gln Ala Ser Ala
            115                 120                 125

Thr Ser Gln Ser Thr Ile Pro Met Ala Pro Ser Ala Thr Pro Ser Asp
            130                 135                 140

Val Pro Thr Thr Pro Leu Ala Ser Ala Lys Pro Asp Ser Phe Val Thr
145                 150                 155                 160

Ala Ser Ser Glu Leu Thr Ser Ser Thr Asn Asp Val Ser Thr Glu Leu
                165                 170                 175

Ser Ser Glu Ser Gln Lys Gln Pro Glu Val Pro Gln Glu Ala Glu Pro
            180                 185                 190

Thr Pro Lys Ala Ala Glu Ser Thr Glu Val Glu Pro Lys Thr Asp Ile
            195                 200                 205

Ser Glu Asp Ser Thr Ser Ala Asn Arg Pro Val Pro Asn Gly Ser Ala
210                 215                 220

Ser Glu Glu Ala Ser Ser Ala Ala Pro Ala Gln Ala Pro Ala Glu Lys
225                 230                 235                 240

Glu Glu Thr Ser Gln Met Leu Thr Ala Pro Ala Ala Gln Lys Ala Val
                245                 250                 255

Ala Asp Thr Thr Ser Val Ala Thr Ser Asn Gly Leu Ser Tyr Ala Pro
            260                 265                 270

Asn His Ala Tyr Asn Pro Met Asn Ala Gly Leu Gln Pro Gln Thr Ala
            275                 280                 285

Ala Phe Lys Glu Glu Val Leu Leu Pro Leu Val Leu Arg His Leu Val
            290                 295                 300

Val Thr Val Gln Glu Ile Gln Glu Ile Ile Gly Lys Gly Leu Ala Ile
305                 310                 315                 320

Asp Phe Met Val Pro Val Ser Ser Thr Leu Gly Asp Gln Val Ala Gln
                325                 330                 335

Tyr Ala Ile Asp His Met Ala Asp Gly Gly Ile Ser Tyr Val Ile Trp
            340                 345                 350

Lys Gln Arg Phe Tyr Ala Pro Phe Ala Ser Ile Tyr Gly Pro Ala Tyr
            355                 360                 365

Thr Trp Asn Pro Met Pro Asp Arg Gly Ser Ile Thr Val Phe His Tyr
            370                 375                 380

Asp His Val His Val Ser Phe Asn Ala
385                 390

<210> SEQ ID NO 32
<211> LENGTH: 1170
<212> TYPE: DNA
<213> ORGANISM: Streptococcus pyogenes

<400> SEQUENCE: 32
```

```
atgattatta ctaaaaagag cttatttgtg acaagtgtcg ctttgtcgtt agtacctttg    60
gcgacagcgc aggcacaaga gtggacacca cgatcggtta cagaaatcaa gtctgaactc   120
gtcctagttg ataatgtttt tacttatact gtaaaatacg gtgacacttt aagcacaatt   180
gctgaagcaa tggggattga tgtgcatgtc ttaggagata ttaatcatat tgctaatatt   240
gacctaattt ttccagacac gatcctaaca gcaaactaca atcaacacgg tcaggcaacg   300
aatttgacgg ttcaagcacc tgcttctagt ccagctagcg ttagtcatgt acctagcagt   360
gagccattac cccaagcatc tgccacctct caaccgactg ttcctatggc accacctgcg   420
acaccatctg atgtcccaac gacaccattc gcatctgcaa agccagatag ttctgtgaca   480
gcgtcatctg agctcacatc gtcaacgaat gatgtttcga ctgagttgtc tagcgaatca   540
caaaagcagc cagaagtacc acaagaagca gttccaactc ctaaagcagc tgaaacgact   600
gaagtcgaac ctaagacaga catctcagaa gccccaactt cagctaatag gcctgtacct   660
aacgagagtg cttcagaaga gtttcttct gcggccccag cacaagcccc agcagaaaaa   720
gaagaaacct ctgcgccagc agcacaaaaa gctgtagctg acaccacaag tgttgcaacc   780
tcaaatggcc tttcttacgc tccaaaccat gcctacaatc aatgaatgc agggcttcaa   840 ccacaaacag cagccttcaa agaagaagtg gcttctgcct ttggtattac gtcatttagt   900
ggttaccgtc caggtgatcc aggagatcat ggtaaaggtt tggccattga ttttatggtg   960
cctgaaaatt ctgctcttgg tgatcaagtt gctcaatatg ccattgacca tatggcagag  1020
cgtggtattt catacgttat ttggaaacag cgattctatg cgccatttgc aagtatttac  1080
ggaccagcct acacatggaa ccccatgcca gatcgcggca gtattacaga aaaccattat  1140
gatcatgttc atgtctcctt taatgcttaa                                   1170
```

<210> SEQ ID NO 33
<211> LENGTH: 389
<212> TYPE: PRT
<213> ORGANISM: Streptococcus pyogenes

<400> SEQUENCE: 33

```
Met Ile Ile Thr Lys Lys Ser Leu Phe Val Thr Ser Val Ala Leu Ser
  1               5                  10                  15

Leu Val Pro Leu Ala Thr Ala Gln Ala Gln Glu Trp Thr Pro Arg Ser
                 20                  25                  30

Val Thr Glu Ile Lys Ser Glu Leu Val Leu Val Asp Asn Val Phe Thr
             35                  40                  45

Tyr Thr Val Lys Tyr Gly Asp Thr Leu Ser Thr Ile Ala Glu Ala Met
         50                  55                  60

Gly Ile Asp Val His Val Leu Gly Asp Ile Asn His Ile Ala Asn Ile
 65                  70                  75                  80

Asp Leu Ile Phe Pro Asp Thr Ile Leu Thr Ala Asn Tyr Asn Gln His
                 85                  90                  95

Gly Gln Ala Thr Asn Leu Thr Val Gln Ala Pro Ala Ser Ser Pro Ala
            100                 105                 110

Ser Val Ser His Val Pro Ser Ser Glu Pro Leu Pro Gln Ala Ser Ala
        115                 120                 125

Thr Ser Gln Pro Thr Val Pro Met Ala Pro Pro Ala Thr Pro Ser Asp
    130                 135                 140

Val Pro Thr Thr Pro Phe Ala Ser Ala Lys Pro Asp Ser Ser Val Thr
145                 150                 155                 160

Ala Ser Ser Glu Leu Thr Ser Ser Thr Asn Asp Val Ser Thr Glu Leu
```

-continued

```
            165                 170                 175
Ser Ser Glu Ser Gln Lys Gln Pro Glu Val Pro Gln Glu Ala Val Pro
        180                 185                 190

Thr Pro Lys Ala Ala Glu Thr Thr Glu Val Glu Pro Lys Thr Asp Ile
    195                 200                 205

Ser Glu Ala Pro Thr Ser Ala Asn Arg Pro Val Pro Asn Glu Ser Ala
210                 215                 220

Ser Glu Glu Val Ser Ser Ala Ala Pro Ala Gln Ala Pro Ala Glu Lys
225                 230                 235                 240

Glu Glu Thr Ser Ala Pro Ala Ala Gln Lys Ala Val Ala Asp Thr Thr
            245                 250                 255

Ser Val Ala Thr Ser Asn Gly Leu Ser Tyr Ala Pro Asn His Ala Tyr
            260                 265                 270

Asn Pro Met Asn Ala Gly Leu Gln Pro Gln Thr Ala Ala Phe Lys Glu
        275                 280                 285

Glu Val Ala Ser Ala Phe Gly Ile Thr Ser Phe Ser Gly Tyr Arg Pro
    290                 295                 300

Gly Asp Pro Gly Asp His Gly Lys Gly Leu Ala Ile Asp Phe Met Val
305                 310                 315                 320

Pro Glu Asn Ser Ala Leu Gly Asp Gln Val Ala Gln Tyr Ala Ile Asp
            325                 330                 335

His Met Ala Glu Arg Gly Ile Ser Tyr Val Ile Trp Lys Gln Arg Phe
            340                 345                 350

Tyr Ala Pro Phe Ala Ser Ile Tyr Gly Pro Ala Tyr Thr Trp Asn Pro
        355                 360                 365

Met Pro Asp Arg Gly Ser Ile Thr Glu Asn His Tyr Asp His Val His
    370                 375                 380

Val Ser Phe Asn Ala
385

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Illustrative
      DNA insert

<400> SEQUENCE: 34
ctgatgtccc aacgacacca t                                              21

<210> SEQ ID NO 35
<211> LENGTH: 12
<212> TYPE: DNA
<213> ORGANISM: Artificial Sequence
<220> FEATURE:
<223> OTHER INFORMATION: Description of Artificial Illustrative
      DNA insert

<400> SEQUENCE: 35
cagatgttaa ct                                                        12

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Illustrative
      amino acid insert
```

```
-continued

<400> SEQUENCE: 36

Ser Asp Val Pro Thr Thr Pro
1               5

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Illustrative
      amino acid insert

<400> SEQUENCE: 37

Glu Thr Ser Gln
1
```